US012721594B2

(12) United States Patent
Takagi et al.

(10) Patent No.: US 12,721,594 B2
(45) Date of Patent: Sep. 1, 2026

(54) ULTRASONIC DIAGNOSTIC APPARATUS

(71) Applicant: Canon Kabushiki Kaisha, Tokyo (JP)

(72) Inventors: Masashi Takagi, Nasushiobara (JP); Takahiro Kano, Utsunomiya (JP); Shingo Toyoda, Utsunomiya (JP); Hideo Onodera, Nasushiobara (JP); Shinichiro Kikuchi, Otawara (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 18/804,542

(22) Filed: Aug. 14, 2024

(65) Prior Publication Data

US 2025/0064428 A1 Feb. 27, 2025

(30) Foreign Application Priority Data

Aug. 22, 2023 (JP) ................................ 2023-134857

(51) Int. Cl.
*A61B 8/00* (2006.01)
*F16M 11/12* (2006.01)

(52) U.S. Cl.
CPC ............ *A61B 8/4405* (2013.01); *A61B 8/469* (2013.01); *F16M 11/121* (2013.01); *F16M 2200/066* (2013.01)

(58) Field of Classification Search
CPC ....... A61B 8/467; A61B 8/469; A61B 8/4405; F16M 2200/066
See application file for complete search history.

(56) References Cited

U.S. PATENT DOCUMENTS

| | | | | |
|---|---|---|---|---|
| 10,709,420 | B2 * | 7/2020 | Woo | A61B 8/467 |
| 10,940,221 | B2 * | 3/2021 | Canfield | A61L 2/10 |
| 2008/0161672 | A1 * | 7/2008 | Marar | A61B 8/00 600/407 |
| 2011/0201927 | A1 * | 8/2011 | Hayakawa | A61B 8/46 600/437 |
| 2013/0197364 | A1 * | 8/2013 | Han | A61B 8/14 600/440 |
| 2015/0105660 | A1 * | 4/2015 | Ninomiya | A61B 8/4427 600/437 |
| 2015/0223892 | A1 * | 8/2015 | Miller | A61B 50/18 345/174 |

(Continued)

FOREIGN PATENT DOCUMENTS

| | | | |
|---|---|---|---|
| JP | 6-133970 | A | 5/1994 |
| JP | WO2014/103720 | A1 | 7/2014 |

(Continued)

*Primary Examiner* — Terrell L Mckinnon
*Assistant Examiner* — Ding Y Tan
(74) *Attorney, Agent, or Firm* — Oblon, McClelland, Maier & Neustadt, L.L.P.

(57) ABSTRACT

An ultrasonic diagnostic apparatus according to an embodiment includes an operation panel, a first support, and a second support. The operation panel is configured to receive a user's operation. The first support includes a rotator that is configured to be rotatable so as to change the height of the operation panel. The first support is configured to support the operation panel. The second support includes a linear motion part that is configured to be linearly movable so as to change the height of the operation panel. The second support is configured to support the first support.

19 Claims, 27 Drawing Sheets

(56) References Cited

U.S. PATENT DOCUMENTS

2015/0342562 A1* 12/2015 Messina ................. F16M 11/10
248/124.1
2015/0351719 A1* 12/2015 Ninomiya ................. B62B 3/10
312/7.2
2017/0027541 A1* 2/2017 Henderson ........... A61B 8/4405
2018/0028160 A1* 2/2018 Cho ....................... A61B 90/50
2018/0368806 A1* 12/2018 Toyoda .................... A61B 8/54
2019/0274660 A1* 9/2019 Cho ..................... F16M 11/046
2020/0237348 A1* 7/2020 Kim ..................... A61B 8/4405
2022/0054107 A1* 2/2022 Onodera .............. A61B 8/4405
2022/0079562 A1* 3/2022 Nakajima .............. A61B 8/467

FOREIGN PATENT DOCUMENTS

JP 2022-47654 A 3/2022
WO WO-2006111874 A2 * 10/2006 ............. A61B 8/462

* cited by examiner 1
4
3
13
7
12
6
11
5
14
71
91
9
92
Z
X
Y
S5:YES
S4

ULTRASONIC DIAGNOSTIC APPARATUS

CROSS REFERENCE TO RELATED APPLICATIONS

This application is based upon and claims the benefit of priority from the prior Japanese Patent Application No. 2023-134857, filed on Aug. 22, 2023, the entire contents of which are incorporated herein by reference.

FIELD

Embodiments disclosed in the present specification and drawings relate to an ultrasonic diagnostic apparatus.

BACKGROUND

An ultrasonic diagnostic apparatus is provided with a linear motion lifting mechanism or an arm lifting mechanism as a device for adjusting the height of an operation panel. The linear motion lifting mechanism moves in the vertical direction and does not move in the depth direction of the operation panel. Therefore, the linear motion lifting mechanism can eliminate an amount of movement of the operation panel in the depth direction, and can reduce a depth dimension of the ultrasonic diagnostic apparatus. However, in a case where the linear motion lifting mechanism is provided in the ultrasonic diagnostic apparatus having a low height, an adjustment range of the height of the operation panel by the lifting mechanism becomes small. On the other hand, in the arm lifting mechanism, the adjustment range of the height of the operation panel can be increased by increasing a length of the arm. However, in the arm lifting mechanism, the depth dimension of the ultrasonic diagnostic apparatus increases in proportion to the length of the arm. In addition, the amount of movement of the operation panel in the depth direction accompanying the movement of the lifting mechanism in the vertical direction also increases.

DETAILED DESCRIPTION

Figure 1:
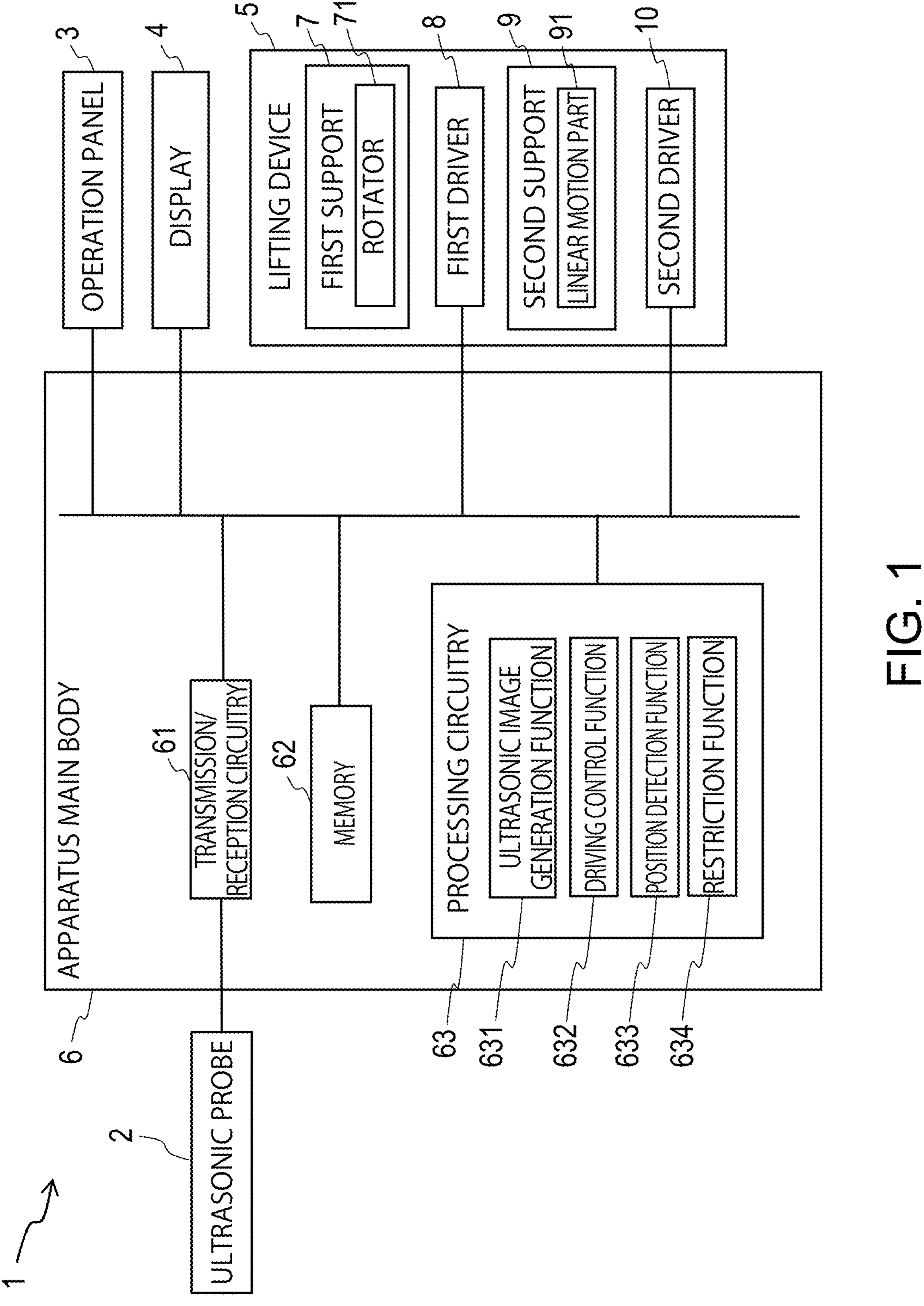
FIG. 1 is a block diagram illustrating a configuration example of an ultrasonic diagnostic apparatus according to a first embodiment.

Hereinafter, an embodiment of an ultrasonic diagnostic apparatus will be described with reference to the drawings. It is noted that, in the following description, components having substantially the same functions and configurations are denoted by the same reference numerals, and a redundant description will be made only when necessary.

First Embodiment

Figure 2A:
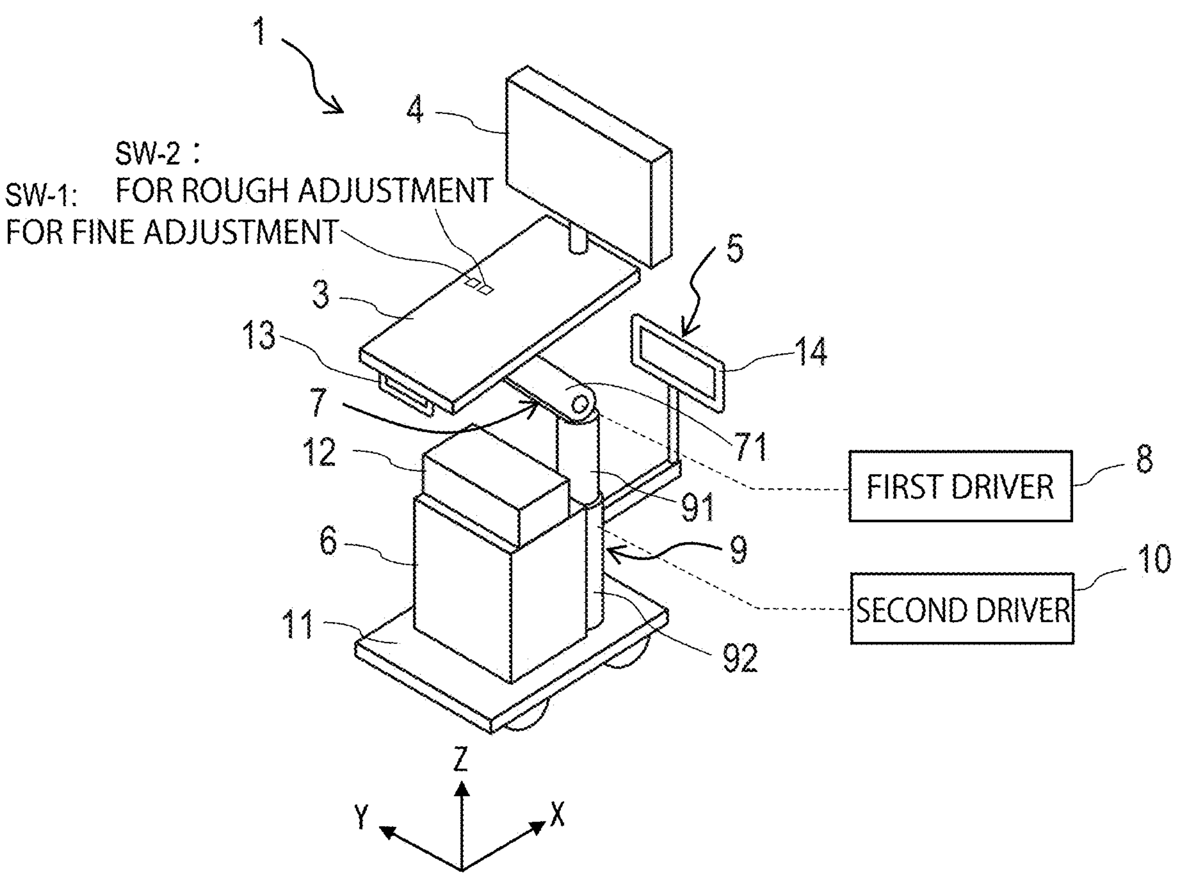
FIG. 2A is a perspective view illustrating the configuration example of the ultrasonic diagnostic apparatus according to the first embodiment.
Figure 2B:
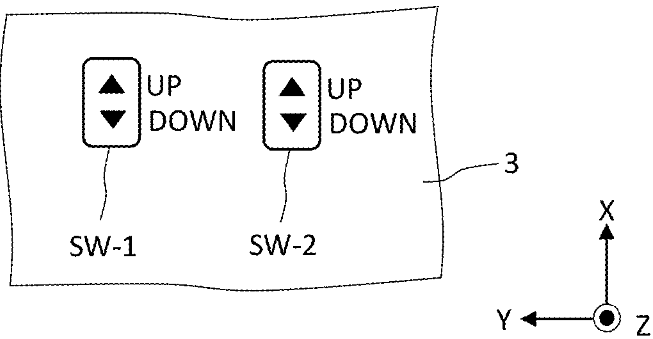
FIG. 2B is a plan view illustrating a configuration example of an operation panel of the ultrasonic diagnostic apparatus according to the first embodiment.
Figure 3:
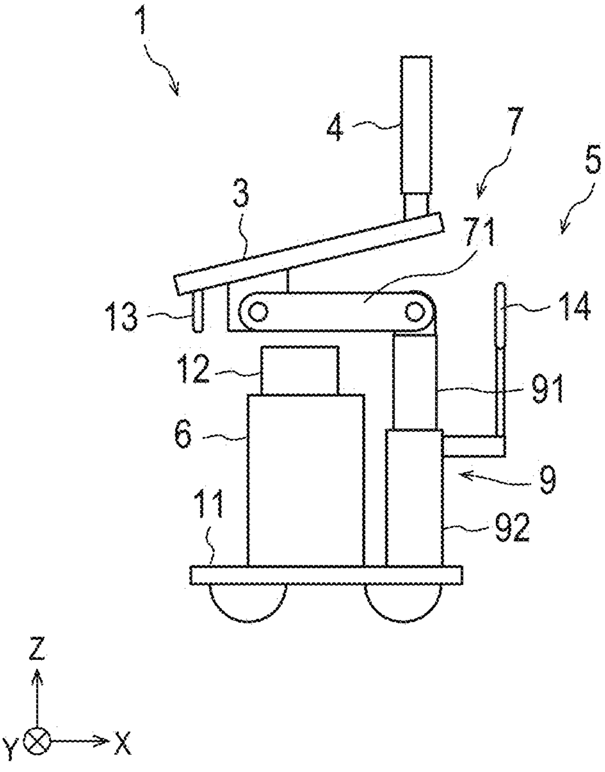
FIG. 3 is a side view illustrating the configuration example of the ultrasonic diagnostic apparatus according to the first embodiment.

FIG. 1 is a block diagram illustrating a configuration example of an ultrasonic diagnostic apparatus 1 according to a first embodiment. FIG. 2A is a perspective view illustrating the configuration example of the ultrasonic diagnostic apparatus 1 according to the first embodiment. FIG. 2B is a plan view illustrating a configuration example of an operation panel 3 of the ultrasonic diagnostic apparatus 1 according to the first embodiment. FIG. 2B is a partially enlarged view of FIG. 2A. FIG. 3 is a side view illustrating the configuration example of the ultrasonic diagnostic apparatus 1 according to the first embodiment. In FIGS. 2A to 3, the X direction is a depth direction of the ultrasonic diagnostic apparatus 1 (hereinafter, the same shall apply). The Y direction is a width direction of the ultrasonic diagnostic apparatus 1 (hereinafter, the same shall apply). The Z direction is a height direction of the ultrasonic diagnostic apparatus 1 (hereinafter, the same shall apply).

As illustrated in FIG. 1, the ultrasonic diagnostic apparatus 1 according to the first embodiment includes an ultrasonic probe 2, the operation panel 3, a display 4, a lifting device 5, and an apparatus main body 6. The ultrasonic probe 2, the operation panel 3, the display 4, and the lifting device 5 are communicably connected to the apparatus main body 6. As illustrated in FIGS. 2A and 3, the ultrasonic diagnostic apparatus 1 further includes a base 11, a peripheral device 12, a front handle 13, and a rear handle 14. The apparatus main body 6 is installed on the horizontal base 11. The peripheral device 12 is installed on the apparatus main body 6. The peripheral device 12 is, for example, a recording/reproducing device such as a printer and a DVD recorder. The lifting device 5 is provided on the base 11 on the rear side (X direction) of the apparatus main body 6. The operation panel 3 is provided on the lifting device 5. The display 4 is provided on the operation panel 3. The front handle 13 is provided at the front end of the operation panel 3. The rear handle 14 is provided at the rear end of the lifting device 5.

The ultrasonic probe 2 is a device that transmits an ultrasonic wave to a subject and receives a reflected wave (echo) of the ultrasonic wave from the subject in order to acquire an ultrasonic image of the subject.

The ultrasonic probe 2 includes a plurality of vibrators. The plurality of vibrators generate an ultrasonic wave based on a driving signal such as a voltage supplied from the apparatus main body 6. The ultrasonic probe 2 receives a reflected wave from the subject and converts the reflected wave into an electrical signal. That is, the ultrasonic probe 2 scans the subject with the ultrasonic wave and receives the reflected wave from the subject. The vibrator is provided with an electrode for supplying the driving signal and inputting the electrical signal of the reflected wave. The vibrator may include, for example, lead zirconate titanate (PZT) and polyvinylidene fluoride (PVDF). For example, an acoustic matching layer and an acoustic lens are disposed on the surface of the vibrator. For example, a backing material is disposed on the back surface of the vibrator. The acoustic matching layer is also called a λ/4 layer, and is a layer for efficiently transmitting and receiving the ultrasonic wave by reducing an impedance difference between the vibrator and a living body. The acoustic lens is a structure for reducing friction with a living body surface at the time of inspection and for improving slice resolution by converging an ultrasonic beam. The backing material has a structure that absorbs a rearward ultrasonic wave and shortens a pulse width of a forward ultrasonic wave. The ultrasonic probe 2 is detachably connected to the apparatus main body 6.

When the ultrasonic wave is transmitted from the ultrasonic probe 2 to the subject, the transmitted ultrasonic wave is reflected one after another on the discontinuous surface of acoustic impedance in a body tissue of the subject, and is received as a reflected wave signal by the plurality of vibrators included in the ultrasonic probe 2. The amplitude of the received reflected wave signal depends on a difference in acoustic impedance at the discontinuous surface from which the ultrasonic wave is reflected. It is noted that the reflected wave signal in a case where the transmitted ultrasonic pulse is reflected by a moving blood flow or the surface of a heart wall or the like receives frequency shift depending on a velocity component with respect to an ultrasonic transmission direction of a moving body due to the Doppler effect.

The ultrasonic probe 2 can be applied to a 1D array probe that scans a subject in a two-dimensional manner, or a three-dimensional probe that scans a subject in a three-dimensional manner, that is, a mechanical 4D probe or a 2D array probe.

The operation panel 3 receives input operations such as various instructions and information from a user. That is, the operation panel 3 receives a user's operation. Specifically, the operation panel 3 converts the input operation received from the user into an electrical signal and outputs the electrical signal to the apparatus main body 6. For example, the operation panel 3 is implemented by a trackball, a switch button, a mouse, a keyboard, a touch pad that performs an input operation by touching an operation surface, a touch screen in which a display screen and a touch pad are integrated with each other, a non-contact input circuitry using an optical sensor, a sound input circuitry, and the like. It is noted that the operation panel 3 is not limited to one including physical operation components such as a mouse and a keyboard. For example, electrical signal processing circuitry that receives an electrical signal corresponding to an input operation from an external input device provided separately from the apparatus and outputs the electrical signal to a control circuitry is also included in the example of the operation panel 3.

In the example illustrated in FIGS. 2A and 2B, the operation panel 3 includes a first switch SW-1 and a second switch SW-2. The first switch SW-1 receives an input operation for finely adjusting the height of the operation panel 3 to the increasing side or the decreasing side. Specifically, the first switch SW-1 receives an ON operation to the rising (UP) side for finely adjusting the height of the operation panel 3 to the increasing side. In addition, the first switch SW-1 receives an ON operation to the falling (DOWN) side for finely adjusting the height of the operation panel 3 to the decreasing side. Further, the first switch SW-1 receives an OFF operation for stopping fine adjustment of the height of the operation panel 3. The second switch SW-2 receives an input operation for roughly adjusting the height of the operation panel 3 to the increasing side or the decreasing side. Specifically, the second switch SW-2 receives an ON operation to the rising (UP) side for roughly adjusting the height of the operation panel 3 to the increasing side. In addition, the second switch SW-2 receives an ON operation to the falling (DOWN) side for roughly adjusting the height of the operation panel 3 to the decreasing side. Further, the second switch SW-2 receives an OFF operation for stopping rough adjustment of the height of the operation panel 3. An adjustment amount of the height of the operation panel 3 per unit time by the input operation received by the first switch SW-1 is smaller than an adjustment amount of the height of the operation panel 3 per unit time by the input operation received by the second switch SW-2. Therefore, the height of the operation panel 3 can be finely adjusted by turning on the first switch SW-1 to the rising side or the falling side. Further, by turning on the second switch SW-2 to the rising side or the falling side, the height of the operation panel 3 can be quickly adjusted.

The display 4 converts information and image data transmitted from the apparatus main body 6 into an electrical signal for display, and outputs the electrical signal. The display 4 is implemented by a liquid crystal monitor, a cathode ray tube (CRT) monitor, a touch panel, and the like. The display 4 may include a speaker. The speaker outputs a predetermined sound such as a beep sound to notify a user of a processing status of the apparatus main body 6.

The lifting device 5 is a device that lifts and lowers the operation panel 3. In the first embodiment, the lifting device 5 lifts and lowers the operation panel 3 in response to the input operation received by the operation panel 3. The lifting device 5 includes a first support 7, a first driver 8, a second support 9, and a second driver 10. The first driver 8 and the second driver 10 are examples of a driver.

The first support 7 includes a rotator 71 that rotates so as to be able to change the height of the operation panel 3. The first support 7 supports the operation panel 3. The first support 7 is located above the peripheral device 12. In the example illustrated in FIGS. 2A and 3, the rotator 71 has an arm shape extending from one end on the second support 9 side to the other end on the operation panel 3 side. One end of the rotator 71 is rotatably connected to the second support 9. That is, the rotator 71 is provided at a position connected to the second support 9. The other end of the rotator 71 is connected to the operation panel 3. The rotator 71 rotates around one end thereof connected to the second support 9 to vertically move the operation panel 3 connected to the other end of the rotator 71 while rotating the operation panel 3. By vertically moving the operation panel 3 while rotating the operation panel 3, the height of the operation panel 3 can be finely adjusted while maintaining the orientation (that is, inclination) of the operation panel 3. A pair of the rotators 71 may be provided at intervals in the Y direction.

The first driver 8 generates driving force for rotating the rotator 71 under the control of the apparatus main body 6. That is, the first driver 8 electrically drives the rotator 71. The first driver 8 includes, for example, a motor, a driving force transmission member such as a gear that transmits driving force of the motor to the rotator 71, and a driving circuitry of the motor. In the example illustrated in FIG. 2A, the first driver 8 generates driving force when the first switch SW-1 for finely adjusting the height of the operation panel 3 is turned on. Therefore, when the first switch SW-1 is turned on, the rotator 71 can finely adjust the height of the operation panel 3 by rotation thereof by the driving force of the first driver 8. On the other hand, when the first switch SW-1 is turned off, the rotator 71 prohibits fine adjustment of the height of the operation panel 3 by stopping rotation thereof.

The second support 9 has a linear motion part 91 that linearly moves so that the height of the operation panel 3 can be changed. The second support 9 supports the first support 7. In the example illustrated in FIG. 2A, the second support 9 further includes a linear motion support 92.

In the example illustrated in FIG. 2A, the linear motion part 91 is a columnar member extending in the vertical direction. The linear motion part 91 can linearly move in the vertical direction. The rotator 71 is rotatably connected to an upper end of the linear motion part 91. Therefore, when the linear motion part 91 linearly moves upwards, the height of the operation panel 3 connected to the linear motion part 91 with the rotator 71 interposed therebetween can be roughly adjusted to the increasing side. On the other hand, when the linear motion part 91 linearly moves downwards, the height of the operation panel 3 can be roughly adjusted to the decreasing side.

The linear motion support 92 supports the linear motion of the linear motion part 91. The linear motion support 92 is provided so as to extend upwards from the base 11. For example, the linear motion support 92 is a cylindrical member capable of partially accommodating the linear motion part 91. The rear handle 14 is provided at a rear end of the linear motion support 92 so as to extend upwards.

The second driver 10 generates driving force for linearly moving the linear motion part 91 under the control of the apparatus main body 6. That is, the second driver 10 electrically drives the linear motion part 91. The second driver 10 includes, for example, a motor, a driving force transmission member such as a gear that transmits driving force of the motor to the linear motion part 91, and a driving circuitry of the motor. In the example illustrated in FIG. 2A, the second driver 10 generates driving force when the second switch SW-2 for roughly adjusting the height of the operation panel 3 is turned on. Therefore, when the second switch SW-2 is turned on, the linear motion part 91 can roughly adjust the height of the operation panel 3 by linear motion thereof by the driving force of the second driver 10. On the other hand, when the second switch SW-2 is turned off, the linear motion part 91 does not linearly move, thereby prohibiting rough adjustment of the height of the operation panel 3.

Additionally, by independently turning on and off the first switch SW-1 and the second switch SW-2, the linear motion part 91 and the rotator 71 can be operated independently.

As illustrated in FIG. 1, the apparatus main body 6 includes a transmission/reception circuitry 61, a memory 62, and processing circuitry 63.

The transmission/reception circuitry 61 is a circuitry that supplies a driving signal to the ultrasonic probe 2 under the control of the processing circuitry 63. The transmission/reception circuitry 61 is also a circuitry that performs various types of processing on the reflected wave signal received by the ultrasonic probe 2 so as to generate reflected wave data.

The transmission/reception circuitry 61 includes, for example, a pulse generator, a transmission delayer, a pulser, and the like in order to supply the driving signal to the ultrasonic probe 2. The pulse generator repeatedly generates a rate pulse for forming a transmitted ultrasonic wave at a predetermined rate frequency. In addition, the transmission delayer focuses the ultrasonic wave generated from the ultrasonic probe 2 in a beam shape and gives a delay time for each vibrator necessary for determining transmission directivity to each rate pulse generated by the pulse generator. The pulser applies a driving signal (a driving pulse) to the ultrasonic probe 2 at a timing based on the rate pulse to which the delay time is given. That is, the transmission delayer freely and selectively adjusts a transmission direction of the ultrasonic wave transmitted from the vibrator surface by changing the delay time given to each rate pulse.

In addition, the transmission/reception circuitry 61 includes, for example, a preamplifier, an analog/digital (A/D) converter, a reception delayer, an adder, and the like in order to perform various types of processing on the reflected wave signal received by the ultrasonic probe 2 to generate reflected wave data. The preamplifier amplifies the reflected wave signal for each channel. The A/D converter A/D converts the amplified reflected wave signal. The reception delayer gives a delay time necessary for determining reception directivity. The adder performs addition processing of the reflected wave signal processed by the reception delayer so as to generate reflected wave data. By the addition processing of the adder, a reflection component from a direction in response to a reception directivity of the reflected wave signal is emphasized, and a comprehensive beam of ultrasonic transmission and reception is formed by the reception directivity and the transmission directivity. A form of the output signal from the transmission/reception circuitry 61 can be selected from various forms such as a case in which the output signal is a signal including phase information called a radio frequency (RF) signal and a case in which the output signal is amplitude information after envelope detection processing.

In the example illustrated in FIG. 1, the transmission/reception circuitry 61 is disposed in the apparatus main body 6. The transmission/reception circuitry 61 is not limited to being disposed in the apparatus main body 6, and at least a part of the transmission/reception circuitry 61 may be disposed in the ultrasonic probe 2.

The memory 62 is a non-transitory storage device that stores various types of information, and is, for example, a hard disk drive (HDD), an optical disk, a solid state drive (SSD), an integrated circuitry storage device, or the like. The memory 62 stores, for example, a control program for controlling the ultrasonic diagnostic apparatus 1 and various data used for executing the control program. The memory 62 may be a driving device that reads and writes various types of information from and to a portable storage medium such as a compact disc (CD), a digital versatile disc (DVD), and a flash memory, a semiconductor memory element such as a random access memory (RAM), or the like, in addition to the HDD, the SSD, and the like.

The processing circuitry 63 is circuitry that controls the entire operation of the ultrasonic diagnostic apparatus 1 in response to the electrical signal of the input operation input from the operation panel 3. For example, the processing circuitry 63 includes an ultrasonic image generation function 631, a driving control function 632, a position detection function 633, and a restriction function 634. The restriction function 634 is an example of a restrictor.

Here, for example, each processing function executed by the ultrasonic image generation function 631, the driving control function 632, the position detection function 633, and the restriction function 634, which are components of the processing circuitry 63 illustrated in FIG. 1, is recorded in the memory 62 in the form of a program executable by a computer. The processing circuitry 63 is, for example, a processor. The processor constituting the processing circuitry 63 reads each program from the memory 62 and executes the program to implement a function corresponding to each read program. In other words, the processing circuitry 63 in a state of reading each program has each function illustrated in the processing circuitry 63 in FIG. 1.

It is noted that FIG. 1 illustrates a case in which each processing function of the ultrasonic image generation function 631, the driving control function 632, the position detection function 633, and the restriction function 634 is implemented by the single processing circuitry 63, but the embodiment is not limited thereto. For example, the processing circuitry 63 may be configured by combining a plurality of independent processors, and each processor may implement each processing function by executing each program. Furthermore, each processing function of the processing circuitry 63 may be implemented by being appropriately distributed to or integrated into a single or a plurality of processing circuitry.

The ultrasonic image generation function 631 acquires an ultrasonic image of a subject based on a reflected wave of an ultrasonic wave from the subject. Specifically, the ultrasonic image generation function 631 receives a reflected wave signal from the ultrasonic probe 2 via the transmission/reception circuitry 61, and generates the ultrasonic image based on the received reflected wave signal.

For example, the ultrasonic image generation function 631 receives reflected wave data from the transmission/reception circuitry 61, performs logarithmic amplification, envelope detection processing, and the like, and generates data (B-mode data) in which signal intensity is expressed by brightness of luminance. In addition, the ultrasonic image generation function 631 performs frequency analysis on velocity information from the reflected wave data received from the transmission/reception circuitry 61, extracts a blood flow, a tissue, and a contrast medium echo component by the Doppler effect, and generates data (Doppler data) obtained by extracting moving body information such as velocity, dispersion, and power for multiple points. In addition, the ultrasonic image generation function 631 can perform processing on both two-dimensional reflected wave data and three-dimensional reflected wave data. That is, the ultrasonic image generation function 631 generates two-dimensional B-mode data from the two-dimensional reflected wave data, and generates three-dimensional B-mode data from the three-dimensional reflected wave data. In addition, the ultrasonic image generation function 631 generates two-dimensional Doppler data from the two-dimensional reflected wave data, and generates three-dimensional Doppler data from the three-dimensional reflected wave data.

Then, the ultrasonic image generation function 631 generates an ultrasonic image from the generated data. For example, the ultrasonic image generation function 631 generates the two-dimensional B-mode image in which the intensity of the reflected wave is represented by luminance from the two-dimensional B-mode data. In addition, for example, the ultrasonic image generation function 631 generates the two-dimensional Doppler image in which blood flow information is imaged from the two-dimensional Doppler data. The two-dimensional Doppler image is velocity image data representing an average velocity of a blood flow, distributed image data representing a variance value of a blood flow, power image data representing power of a blood flow, or image data obtained by combining the above-mentioned data. In addition, the ultrasonic image generation function 631 generates, as a Doppler image, a color Doppler image in which pieces of blood flow information such as an average velocity, a variance value, and power of a blood flow are displayed in color, or generates a Doppler image in which one piece of blood flow information is displayed in gray scale. Furthermore, for example, the ultrasonic image generation function 631 can also generate an M-mode image from time-series data of B-mode data on one scanning line. Furthermore, the ultrasonic image generation function 631 can also generate a Doppler waveform obtained by plotting a blood flow and tissue velocity information along time series from the Doppler data.

The driving control function 632 controls driving of the rotator 71 by the first driver 8. In addition, the driving control function 632 controls driving of the linear motion part 91 by the second driver 10. In the example illustrated in FIG. 2A, when the first switch SW-1 is turned on, the driving control function 632 causes the first driver 8 to drive the rotator 71 by outputting an electrical signal instructing driving of the rotator 71 to the first driver 8. In addition, when the second switch SW-2 is turned on, the driving control function 632 causes the second driver 10 to drive the linear motion part 91 by outputting an electrical signal instructing driving of the linear motion part 91 to the second driver 10.

The position detection function 633 detects a position of the second support 9 in the linear motion direction (that is, in the height direction). That is, the position detection function 633 detects the position of the linear motion part 91 in the linear motion direction. The position of the second support 9 in the linear motion direction is, for example, a position of a reference point of the second support 9 such as an upper end of the second support 9. The position detection function 633 may detect the position of the second support 9 in the linear motion direction based on the driving amount of the linear motion part 91 by the second driver 10 such as a rotation amount of the motor. Alternatively, the position detection function 633 may detect the position of the second support 9 in the linear motion direction using a sensor such as an optical sensor.

The restriction function 634 restricts the rotation range of the rotator 71 depending on the height of the second support 9 linearly moved by the linear motion part 91. In other words, the restriction function 634 restricts the rotation range of rotator 71 depending on the position of the second support 9 in the linear motion direction. In the first embodiment, the restriction function 634 electrically restricts the rotation range of the rotator 71 based on the position of the second support 9 in the linear motion direction detected by the position detection function 633.

Specifically, when the position of the second support 9 in the linear motion direction is a first position, the restriction function 634 restricts the rotation range of the rotator 71 so that the first support 7 becomes horizontal. The first position is a position of the second support 9 at which the first support 7 is difficult to rotate up to a position lower than the horizontal (that is, a position inclined downwards relative to the horizontal) without coming into contact with a structure below the first support 7 (for example, the peripheral device 12) at this position. In other words, the first position is a position of the second support 9 at which a distance between the first support 7 and the structure below the first support 7 (for example, the peripheral device 12) is equal to or less than a threshold distance when the first support 7 becomes horizontal at this position. The first position is, for example, a position of the second support 9 when the height of the second support 9 is equal to or less than a threshold height. It is noted that the first position is not limited to one position, and may be a plurality of positions over a set range. Further, the structure below the first support 7 may be a structure other than the peripheral device 12, such as the apparatus main body 6.

More specifically, when fine adjustment of the panel height to the decreasing side is instructed by the first switch SW-1, in a case where the position of the second support 9 detected by the position detection function 633 is the first position, the restriction function 634 restricts the driving of the rotator 71 by the first driver 8 so that a position at which the first support 7 becomes horizontal becomes a downward movement limit position of the first support 7.

In addition, when the position of the second support 9 in the linear motion direction is a second position higher than the first position, the restriction function 634 restricts the rotation range of the rotator 71 so as to allow the position of the first support 7 to be located below the horizontal (that is, the first support 7 is inclined downwards relative to the horizontal). The second position is a position of the second support 9 at which the first support 7 can rotate up to a position lower than the horizontal without coming into contact with the structure below the first support 7 (for example, the peripheral device 12) at this position. In other words, the second position is a position of the second support 9 at which the distance between the first support 7 and the structure below the first support 7 (for example, the peripheral device 12) becomes larger than the threshold distance when the first support 7 becomes horizontal at this position. The second position is, for example, a position of the second support 9 when the height of the second support 9 is larger than the threshold height. The second position is a plurality of positions over the set range.

More specifically, when fine adjustment of the panel height to the decreasing side is instructed by the first switch SW-1, in a case where the position of the second support 9 detected by the position detection function 633 is the second position, the restriction function 634 restricts the driving of the rotator 71 by the first driver 8 so that a position at which the first support 7 is located below the horizontal becomes the downward movement limit position of the first support 7.

Regarding a degree to which the first support 7 is located below the horizontal (that is, a degree to which the first support 7 is inclined downwards relative to the horizontal), the restriction function 634 may perform restriction so as to prevent the first support 7 from contacting the structure therebelow. For example, in a case where the position of the second support 9 is a low position among the plurality of second positions over the set range, the driving control function 632 may restrict the rotation range of the rotator 71 so that the rotation of the first support 7 is stopped at a location higher than a location of a case in which the position of the second support 9 is a high position among the plurality of second positions. On the other hand, in a case where the position of the second support 9 is a high position among the plurality of second positions, the driving control function 632 may alleviate the restriction on the rotation range of the rotator 71 so that the first support 7 rotates up to a location lower than a location of a case in which the position of the second support 9 is a low position among the plurality of second positions. Alternatively, regarding the degree to which the first support 7 is located below the horizontal, the restriction function 634 may perform restriction so as to prevent the first support 7 from contacting the operation panel 3. In addition, when the rotator 71 is located below the horizontal, the restriction function 634 may restrict the driving of the linear motion part 91 by the second driver 10 so that the position of the second support 9 does not become equal to or lower than the threshold height.

Figure 4:
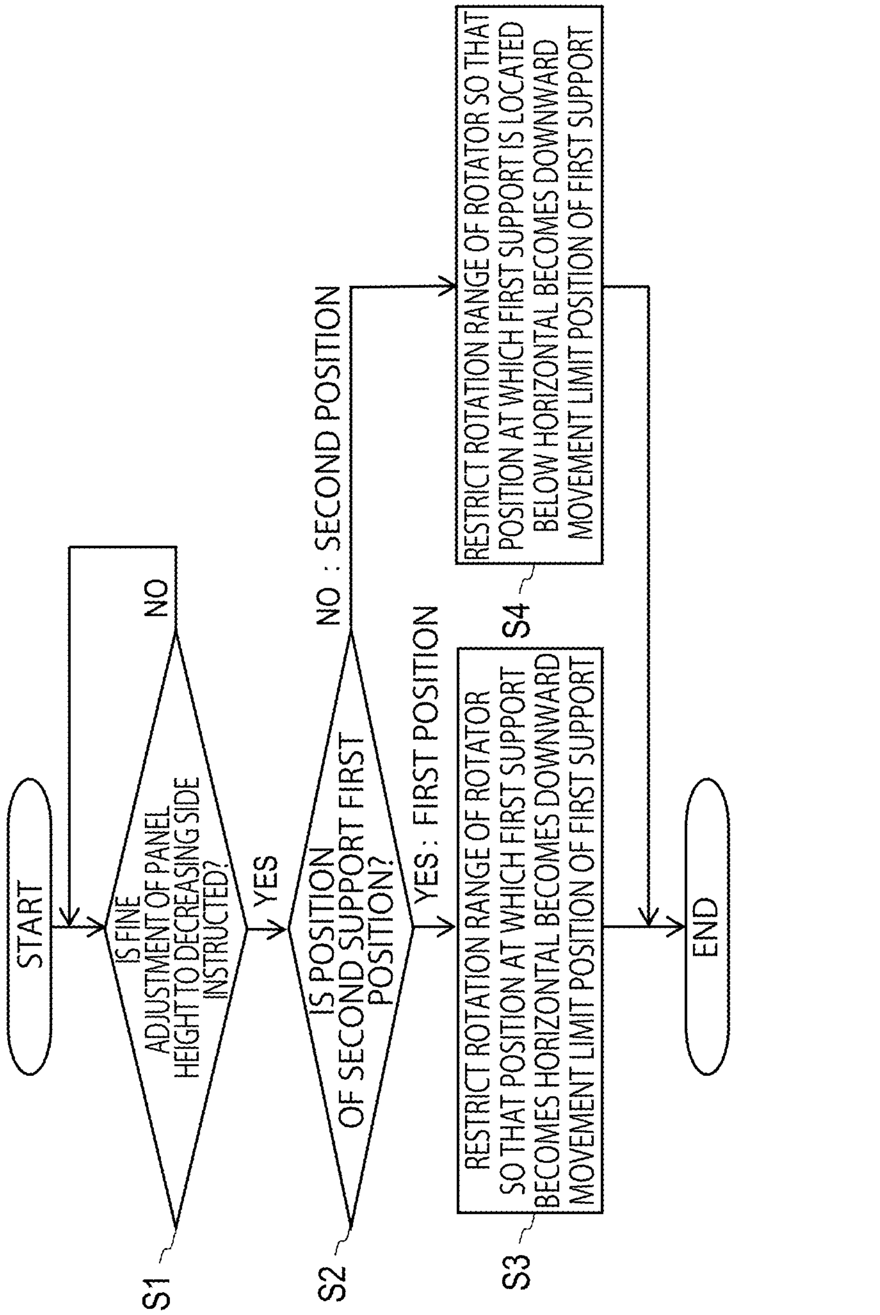
FIG. 4 is a flowchart illustrating an operation example of the ultrasonic diagnostic apparatus according to the first embodiment.

Next, an operation example of the ultrasonic diagnostic apparatus 1 according to the first embodiment configured as described above will be described. FIG. 4 is a flowchart illustrating the operation example of the ultrasonic diagnostic apparatus 1 according to the first embodiment. It is noted that, in the initial state in FIG. 4, the operation panel 3 is raised up to a position corresponding to the rotation of the rotator 71 by the operation of the first switch SW-1 and the linear motion of the linear motion part 91 by the operation of the second switch SW-2.

Then, from the initial state, first, the restriction function 634 determines whether fine adjustment of the panel height to the decreasing side is instructed by the ON operation of the first switch SW-1 to the falling side (step S1).

When the fine adjustment of the panel height to the decreasing side is instructed (step S1: YES), the restriction function 634 determines whether the position of the second support 9 is the first position based on the position of the second support 9 detected by the position detection function 633 (step S2). Here, when the height of the second support 9 is equal to or less than a threshold, the restriction function 634 determines that the position of the second support 9 is the first position. On the other hand, when the height of the second support 9 is equal to or greater than the threshold, the restriction function 634 determines that the position of the second support 9 is the second position.

When the position of the second support 9 is the first position (step S2: YES), the restriction function 634 restricts the rotation range of the rotator 71 so that a position at which the first support 7 becomes horizontal becomes a downward movement limit position of the first support 7 (step S3).

Figure 5:
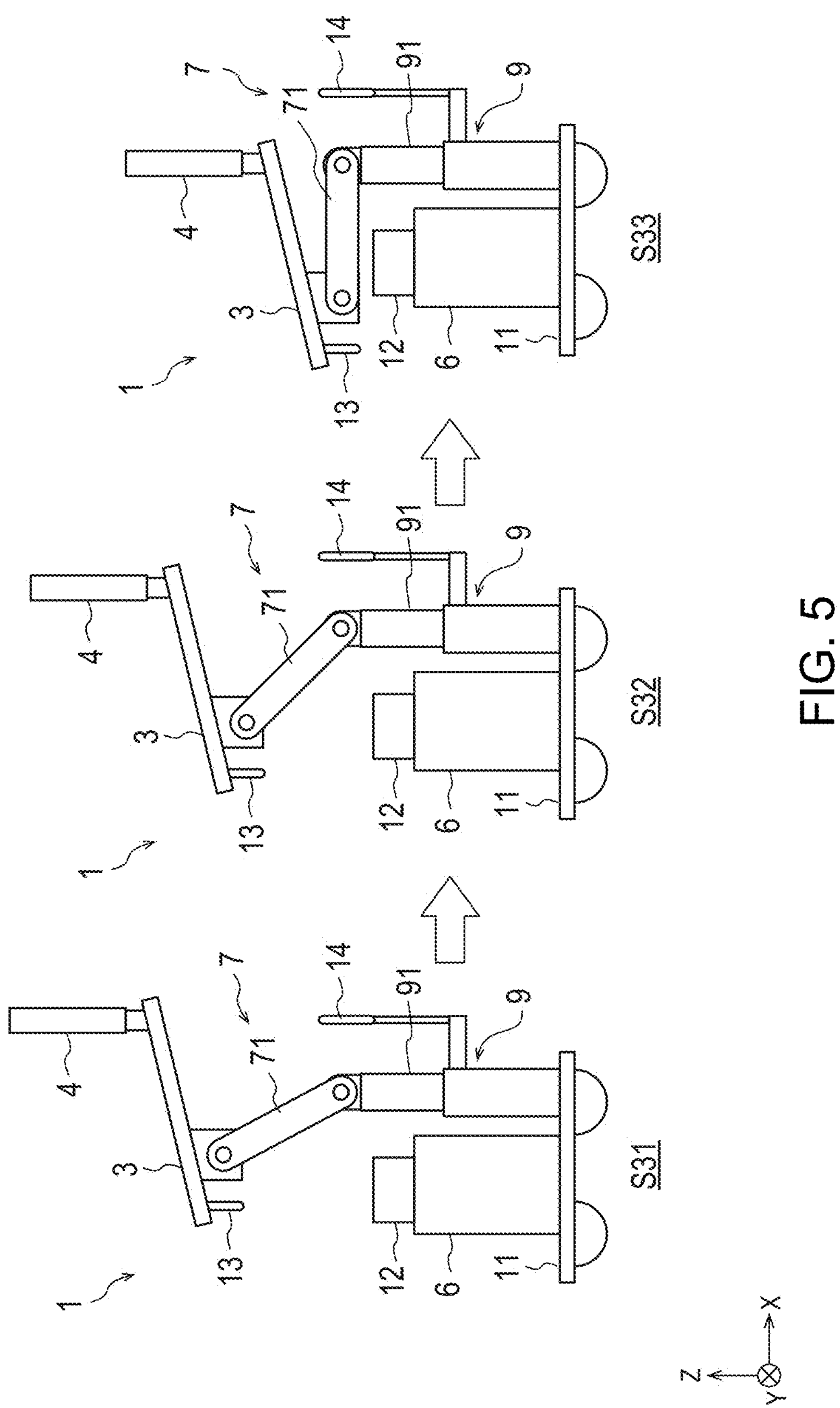
FIG. 5 is a side view illustrating the operation example of the ultrasonic diagnostic apparatus according to the first embodiment.

FIG. 5 is a side view illustrating the operation example of the ultrasonic diagnostic apparatus 1 according to the first embodiment. Specifically, until the rotator 71 becomes horizontal, the restriction function 634 permits control of the first driver 8 by the driving control function 632 for rotating the rotator 71 downwards. Therefore, until the rotator 71 becomes horizontal, the driving control function 632 controls the first driver 8 so that the rotator 71 rotates downwards in response to the operation of the first switch SW-1 (step S31 and step S32). The restriction function 634 may detect that the rotator 71 becomes horizontal based on a driving amount of the first driver 8 acquired in advance. Alternatively, the restriction function 634 may detect that the rotator 71 becomes horizontal using a sensor such as an optical sensor.

When the rotator 71 becomes horizontal, the restriction function 634 stops the control of the first driver 8 by the driving control function 632 for rotating the rotator 71 downwards. Therefore, when the rotator 71 becomes horizontal, the driving control function 632 stops the first driver 8 so that the rotator 71 does not rotate downwards any more regardless of the operation of the first switch SW-1 (step S33). As a result, the position of the first support 7 when the first support 7 becomes horizontal becomes the downward movement limit position of the first support 7.

On the other hand, as illustrated in FIG. 4, when the position of the second support 9 is not the first position, that is, when the position of the second support 9 is the second position (step S2: NO), the restriction function 634 restricts the rotation range of the rotator 71 so that a position at which the first support 7 is located below the horizontal becomes the downward movement limit position of the first support 7 (step S4).

Figure 6:
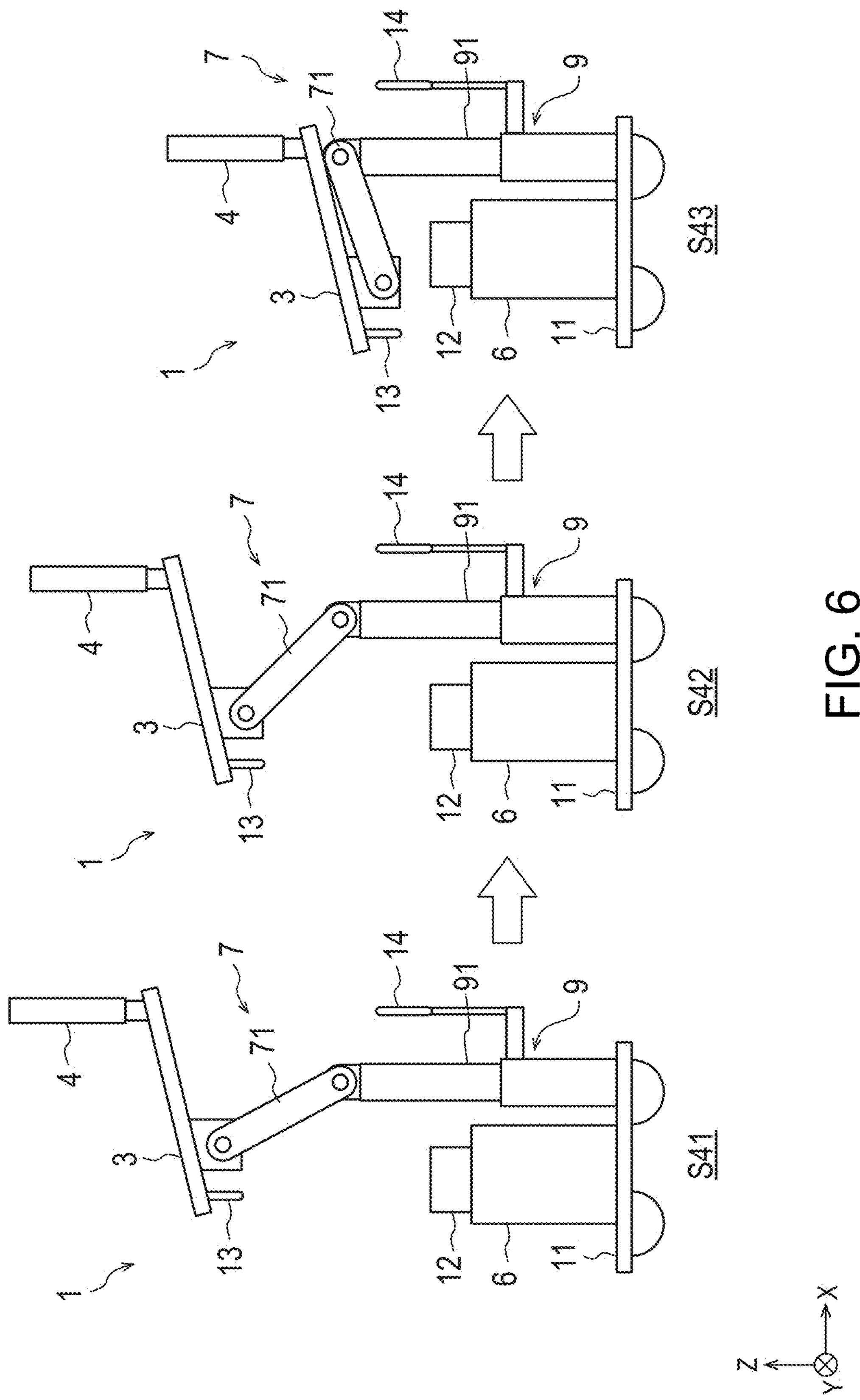
FIG. 6 is a side view illustrating another operation example of the ultrasonic diagnostic apparatus according to the first embodiment.

FIG. 6 is a side view illustrating another operation example of the ultrasonic diagnostic apparatus 1 according to the first embodiment. Specifically, even when the rotator 71 is located below the horizontal, the restriction function 634 does not stop the control of the first driver 8 by the driving control function 632 for rotating the rotator 71 downwards. Therefore, even when the rotator 71 is located below the horizontal, the driving control function 632 controls the first driver 8 so that the rotator 71 rotates downwards in response to the operation of the first switch SW-1 (step S41, step S42, and step S43). The restriction function 634 causes the rotator 71 to rotate downwards from the horizontal to a position at which the rotator 71 does not contact the peripheral device 12. As a result, the position of the first support 7 when the first support 7 is located below the horizontal becomes the downward movement limit position of the first support 7.

As described above, in the first embodiment, the ultrasonic diagnostic apparatus 1 includes the operation panel 3, the first support 7, and the second support 9. The operation panel 3 receives a user's operation. The first support 7 includes the rotator 71 that rotates to change the height of the operation panel 3, and supports the operation panel 3. The second support 9 has the linear motion part 91 that linearly moves so as to change the height of the operation panel 3, and supports the first support 7.

As a result, since the adjustment range of the height of the operation panel 3 by the rotator 71 can be added to the adjustment range of the height of the operation panel 3 by the linear motion part 91, the adjustment range of the height of the operation panel 3 can be increased even when the lifting device 5 is provided in the ultrasonic diagnostic apparatus 1 having a low height. In addition, since the linear motion part 91 is provided, the adjustment range of the height of the operation panel 3 can be increased without increasing the length of the rotator 71, so that the rotator 71 can be shortened. By shortening the rotator 71, the amount of movement of the operation panel 3 in the depth direction accompanying the rotation of the rotator 71 can be reduced. By reducing the amount of movement of the operation panel 3 in the depth direction, the operability of the operation panel 3 can be improved. In addition, by shortening the rotator 71, the depth dimension of the ultrasonic diagnostic apparatus 1 can be reduced. Therefore, the height adjustment range of the operation panel 3 can be expanded, the amount of movement of the operation panel 3 in the depth direction can be reduced, and the depth dimension of the ultrasonic diagnostic apparatus 1 can be reduced.

In the first embodiment, the restriction function 634 restricts the rotation range of the rotator 71 depending on the height of the second support 9 that is linearly moved by the linear motion part 91.

As a result, it is possible to prevent the first support 7 from coming into contact with the peripheral device 12 located on the lower side of the first support 7 due to the rotation of the rotator 71.

In the first embodiment, when the position of the second support 9 in the linear motion direction is the first position, the restriction function 634 restricts the rotation range of the rotator 71 so that the first support becomes horizontal.

As a result, when the height of the second support 9 is low, the rotation range of the rotator 71 is restricted so that the first support 7 becomes horizontal, whereby the first support 7 can be appropriately prevented from contacting the peripheral device 12 located on the lower side of the first support 7.

In the first embodiment, when the position of the second support 9 in the linear motion direction is the second position higher than the first position, the restriction function 634 restricts the rotation range of the rotator 71 so as to allow the first support 7 to be located below the horizontal.

As a result, when the height of the second support 9 is high, the adjustment range of the operation panel 3 can be expanded by restricting the rotation range of the rotator 71 so as to allow the first support 7 to be located below the horizontal.

In the first embodiment, the rotator 71 of the first support 7 is provided at a position connected to the second support 9.

As a result, the depth dimension of the ultrasonic diagnostic apparatus 1 can be reduced as compared with a case in which the rotator 71 is provided at a position shifted from the second support 9 in the depth direction.

In the first embodiment, the rotator 71 and the linear motion part 91 can operate independently.

As a result, a degree of freedom in adjusting the height of the operation panel 3 can be improved.

In the first embodiment, the restriction function 634 electrically restricts the rotation range of the rotator 71.

As a result, an operation burden on a user can be reduced by electrically restricting the rotation range of the rotator 71.

In the first embodiment, the first driver 8 electrically drives the rotator 71. The second driver 10 electrically drives the linear motion part 91.

As a result, the rotator 71 and the linear motion part 91 are electrically driven, so that an operation burden on the user can be reduced.

Second Embodiment

Figure 7:
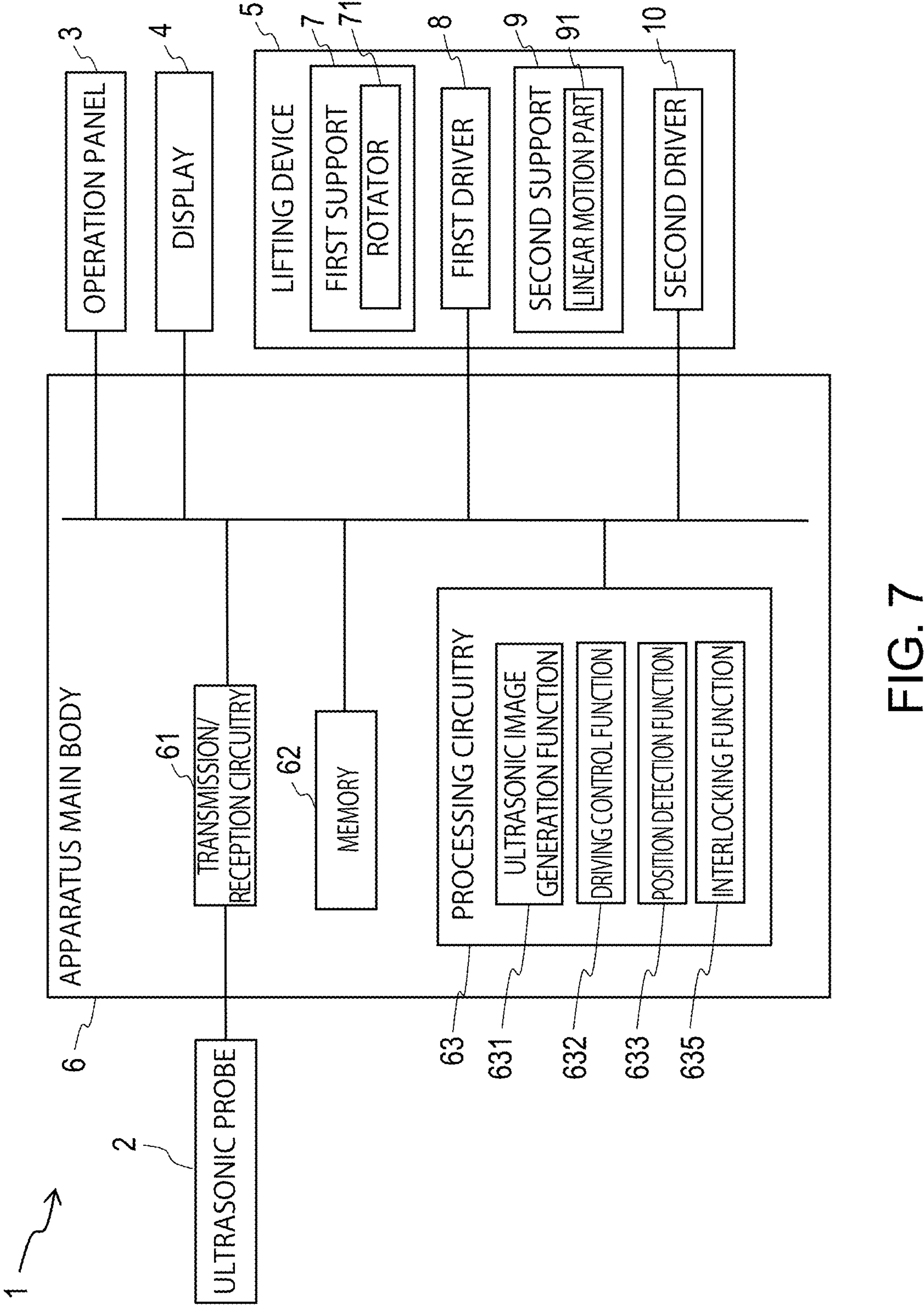
FIG. 7 is a block diagram illustrating a configuration example of an ultrasonic diagnostic apparatus according to a second embodiment.

Next, a second embodiment in which the rotator 71 and the linear motion part 91 are interlocked will be described, focusing on a difference between the first embodiment and the second embodiment. FIG. 7 is a block diagram illustrating a configuration example of an ultrasonic diagnostic apparatus 1 according to the second embodiment.

As illustrated in FIG. 7, the processing circuitry 63 of the ultrasonic diagnostic apparatus 1 according to the second embodiment has an interlocking function 635 instead of the restriction function 634 of the first embodiment. The interlocking function 635 controls the first driver 8 and the second driver 10 so that the rotator 71 and the linear motion part 91 are interlocked with each other. In addition, the interlocking function 635 controls the first driver 8 and the second driver 10 so as to drive one of the rotator 71 and the linear motion part 91 when the other of the rotator 71 and the linear motion part 91 reaches a movement limit.

Figure 8:
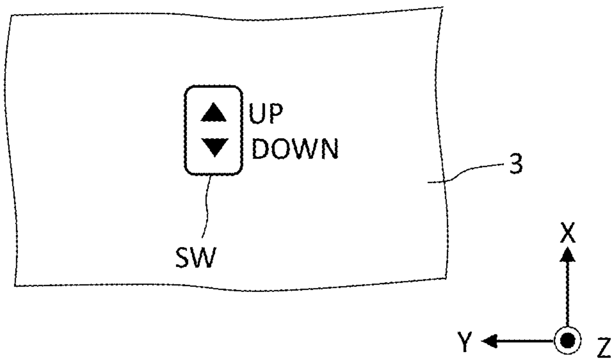
FIG. 8 is a plan view illustrating a configuration example of an operation panel of the ultrasonic diagnostic apparatus according to the second embodiment.

FIG. 8 is a plan view illustrating a configuration example of the operation panel 3 of the ultrasonic diagnostic apparatus 1 according to the second embodiment. As illustrated in FIG. 8, the operation panel 3 includes a common switch SW for interlocking the rotator 71 and the linear motion part 91. The switch SW receives an input operation for adjusting the height of the operation panel 3 to the increasing side or the decreasing side. Specifically, the switch SW receives an ON operation to the rising (UP) side for adjusting the height of the operation panel 3 to the increasing side, an ON operation to the falling (DOWN) side for adjusting the height of the operation panel 3 to the decreasing side, and an OFF operation for stopping the adjustment of the height of the operation panel 3. The switch SW is a switch commonly used for rough adjustment and fine adjustment of the height of the operation panel 3.

Figure 9:
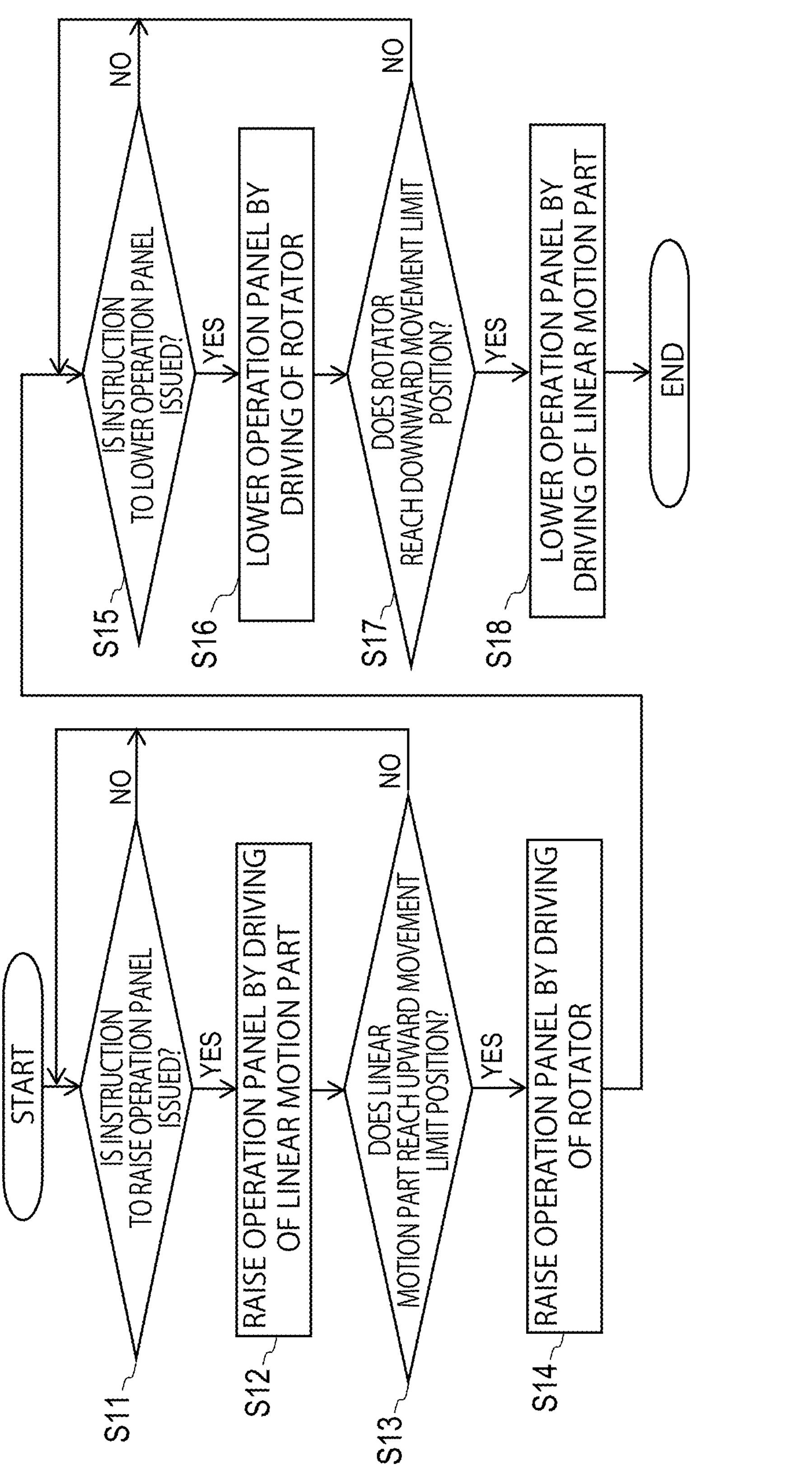
FIG. 9 is a flowchart illustrating an operation example of the ultrasonic diagnostic apparatus according to the second embodiment.
Figure 10:
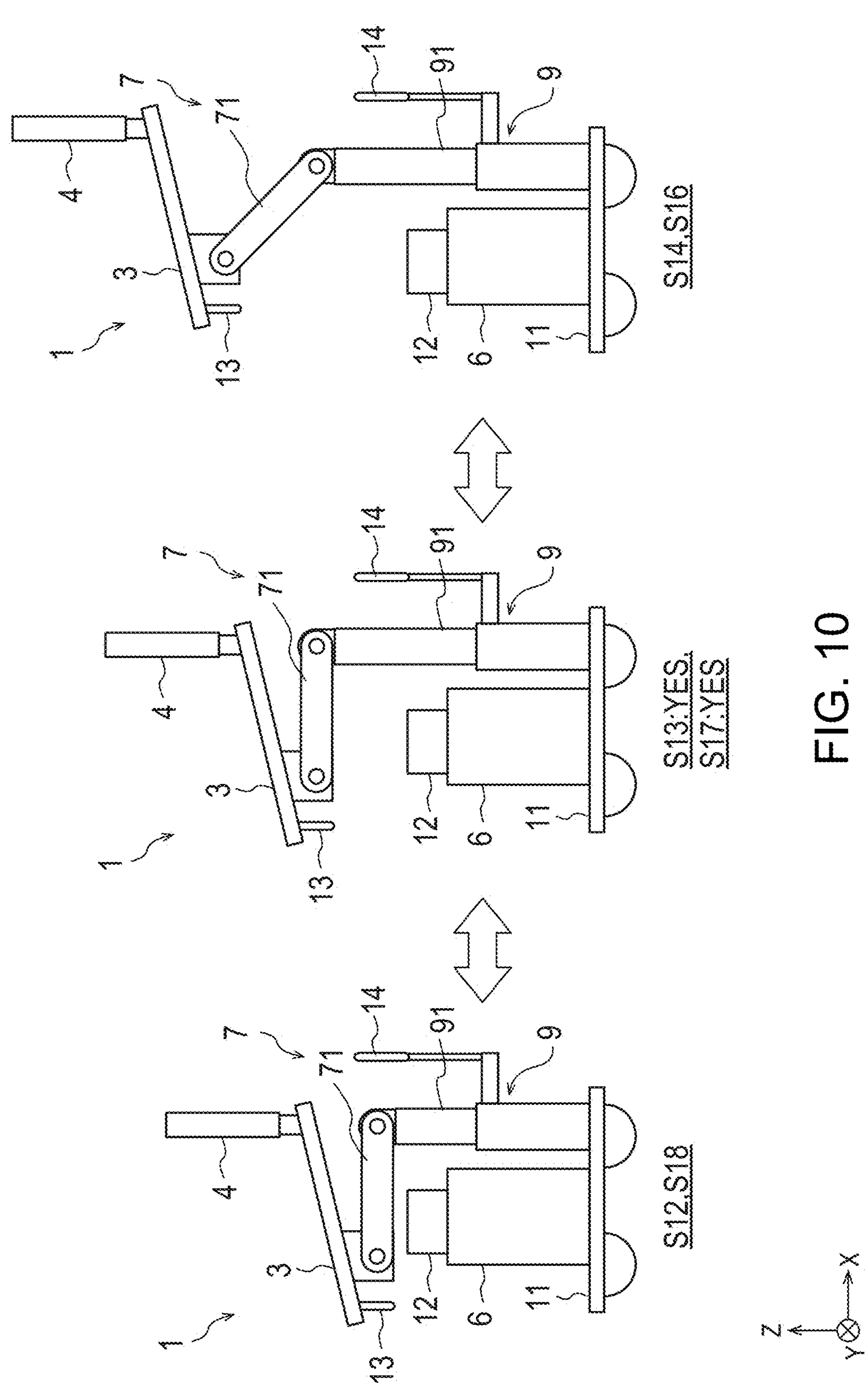
FIG. 10 is a side view illustrating the operation example of the ultrasonic diagnostic apparatus according to the second embodiment.

Next, an operation example of the ultrasonic diagnostic apparatus 1 according to the second embodiment configured as described above will be described. FIG. 9 is a flowchart illustrating the operation example of the ultrasonic diagnostic apparatus 1 according to the second embodiment. FIG. 10 is a side view illustrating the operation example of the ultrasonic diagnostic apparatus 1 according to the second embodiment. It is noted that, in the initial state in FIG. 9, it is assumed that the operation panel 3 is not raised, and the linear motion part 91 and the rotator 71 are positioned at the respective downward movement limit positions.

Then, from the initial state, first, the driving control function 632 determines whether an instruction to raise the operation panel 3 by the ON operation of the switch SW to the rising side is issued (step S11).

When the instruction to raise the operation panel 3 is issued (step S11: YES), the driving control function 632 causes the second driver 10 to drive the linear motion part 91, thereby raising the operation panel 3 (step S12). On the other hand, when the instruction to raise the operation panel 3 is not issued (step S11: NO), the driving control function 632 repeats the determination as to whether the instruction to raise the operation panel 3 is issued (step S11).

After the operation panel 3 is raised, the interlocking function 635 determines whether the linear motion part 91 reaches the upward movement limit position (step S13). For example, the interlocking function 635 may determine whether the linear motion part 91 reaches the upward movement limit position based on the driving amount of the second driver 10. Alternatively, the interlocking function 635 may determine whether the linear motion part 91 reaches the upward movement limit position using a sensor such as an optical sensor.

When the linear motion part 91 reaches the upward movement limit position (step S13: YES), the interlocking function 635 causes the driving control function 632 to switch a control target from the driving of the linear motion part 91 to the driving of the rotator 71. Then, the driving control function 632 causes the first driver 8 to drive the rotator 71 in response to the fact that the ON operation of the switch SW to the rising side is continuously performed, thereby further raising the operation panel 3 (step S14). On the other hand, when the linear motion part 91 does not reach the upward movement limit position (step S13: NO), the driving control function 632 repeats the determination as to whether the instruction to raise the operation panel 3 is issued (step S11).

Therefore, in the second embodiment, as illustrated in FIG. 10, until the linear motion part 91 reaches the upward movement limit position, the operation panel 3 is raised by the linear motion of the linear motion part 91 in response to the ON operation of the switch SW to the rising side. After the linear motion part 91 reaches the upward movement limit position, the operation panel 3 is further raised by the rotation of the rotator 71 in response to the continuous ON operation of the switch SW to the rising side.

After the rising of the operation panel 3 by the linear motion of the linear motion part 91 and the rotation of the rotator 71 is completed, as illustrated in FIG. 9, the driving control function 632 determines whether an instruction to lower the operation panel 3 by the ON operation of the switch SW to the falling side is issued (step S15).

When the instruction to lower the operation panel 3 is issued (step S15: YES), the driving control function 632 causes the first driver 8 to drive the rotator 71, thereby lowering the operation panel 3 (step S16). On the other hand, when the instruction to lower the operation panel 3 is not issued (step S15: NO), the driving control function 632 repeats the determination as to whether the instruction to lower the operation panel 3 is issued (step S15).

After the operation panel 3 is lowered, the interlocking function 635 determines whether the rotator 71 reaches the downward movement limit position (step S17). For example, the interlocking function 635 may determine whether the rotator 71 reaches the downward movement limit position based on the driving amount of the first driver 8. Alternatively, the interlocking function 635 may determine whether the rotator 71 reaches the downward movement limit position using a sensor such as an optical sensor.

When the rotator 71 reaches the downward movement limit position (step S17: YES), the interlocking function 635 causes the driving control function 632 to switch a control target from the driving of the rotator 71 to the driving of the linear motion part 91. Then, the driving control function 632 causes the second driver 10 to drive the linear motion part 91 in response to the fact that the ON operation of the switch SW to the falling side is continuously performed, thereby further lowering the operation panel 3 (step S18). On the other hand, when the rotator 71 does not reach the downward movement limit position (step S17: NO), the driving control function 632 repeats the determination as to whether the instruction to lower the operation panel 3 is issued (step S15).

Therefore, in the second embodiment, as illustrated in FIG. 10, until the rotator 71 reaches the downward movement limit position, the operation panel 3 is lowered by the rotation of the rotator 71 in response to the ON operation of the switch SW to the falling side. After the rotator 71 reaches the downward movement limit position, the operation panel 3 is further lowered by the linear motion of the linear motion part 91 in response to the continuous ON operation of the switch SW to the falling side.

As described above, in the second embodiment, the first driver 8 drives the rotator 71 when the linear motion part 91 reaches the movement limit (that is, the upward movement limit position). Further, the second driver 10 drives the linear motion part 91 when the rotator 71 reaches the movement limit (that is, the downward movement limit position).

As a result, the rotator 71 and the linear motion part 91 can be interlocked with each other in response to a single input operation (that is, the ON operation of the switch SW) for raising or lowering the operation panel 3, thereby making it possible to reduce an operation burden on the user for adjusting the height of the operation panel 3.

Modification of Second Embodiment

Figure 11:
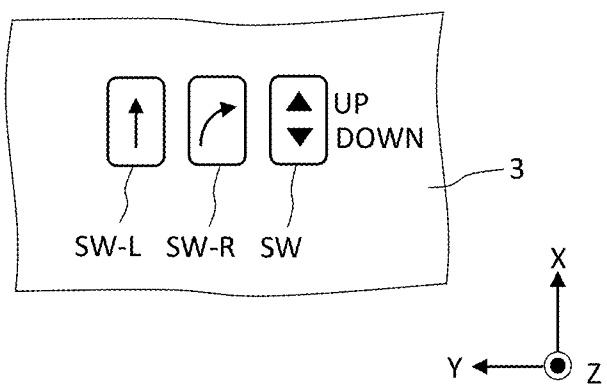
FIG. 11 is a plan view illustrating an operation panel of an ultrasonic diagnostic apparatus according to a modification of the second embodiment.

Next, a modification of the second embodiment capable of designating priority of driving of the rotator 71 and the linear motion part 91 will be described, focusing on a difference between the modification and the second embodiment. FIG. 11 is a plan view illustrating an operation panel 3 of an ultrasonic diagnostic apparatus 1 according to the modification of the second embodiment. As illustrated in FIG. 11, the operation panel 3 of the ultrasonic diagnostic apparatus 1 according to the modification of the second embodiment further includes a first designation switch SW-R that designates an instruction to drive the rotator 71 in preference to the linear motion part 91, and a second designation switch SW-L that designates an instruction to drive the linear motion part 91 in preference to the rotator 71. The first designation switch SW-R and the second designation switch SW-L are an example of a third operation unit that performs an operation to designate which of the rotator 71 and the linear motion part 91 is to be preferentially driven. The driving control function 632 controls the drivers 8 and 10 so as to preferentially drive one of the rotator 71 and the linear motion part 91 designated by the designation switches SW-R and SW-L.

Figure 12:
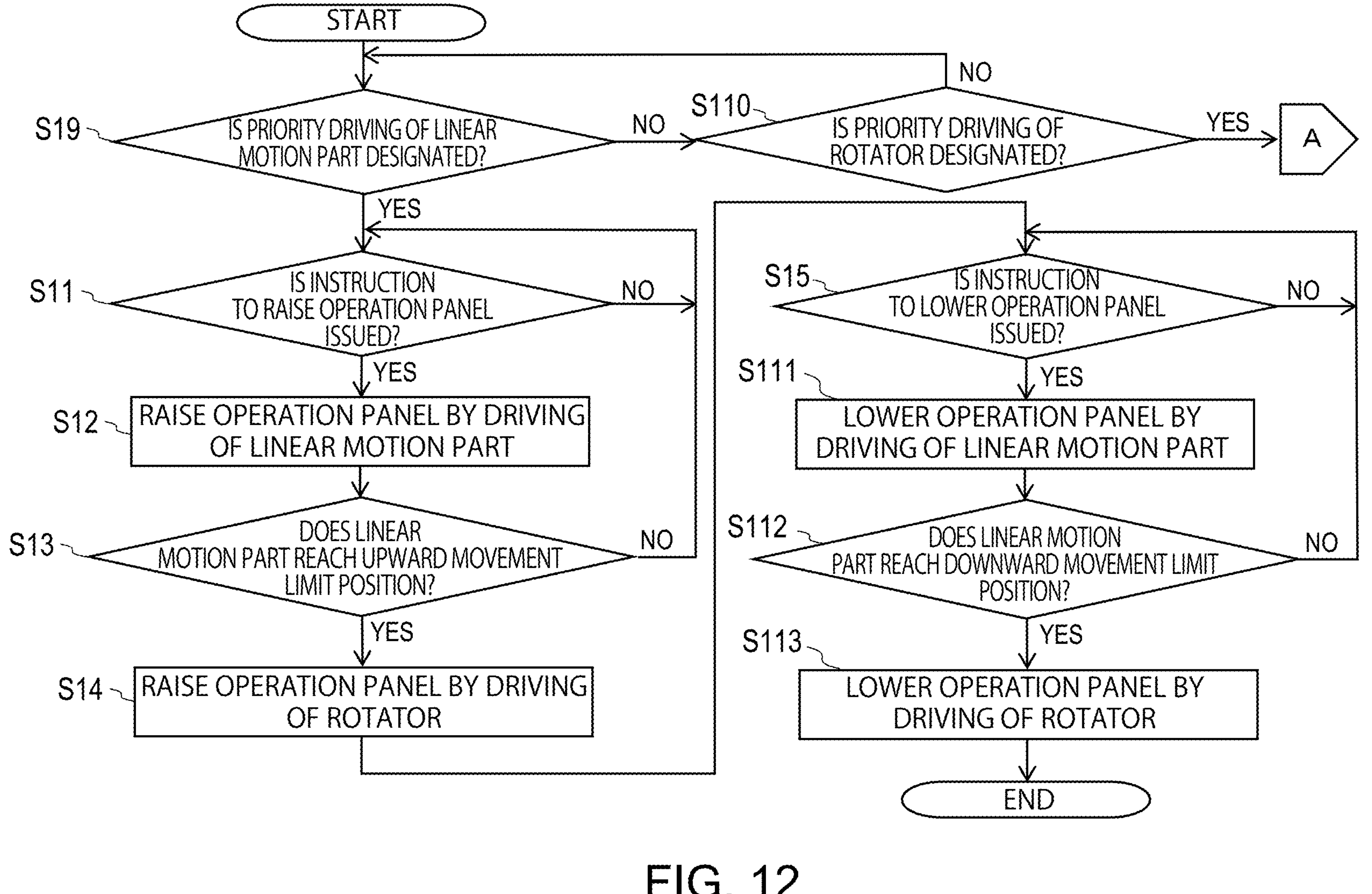
FIG. 12 is a flowchart illustrating an operation of the ultrasonic diagnostic apparatus according to the modification of the second embodiment.
Figure 13:
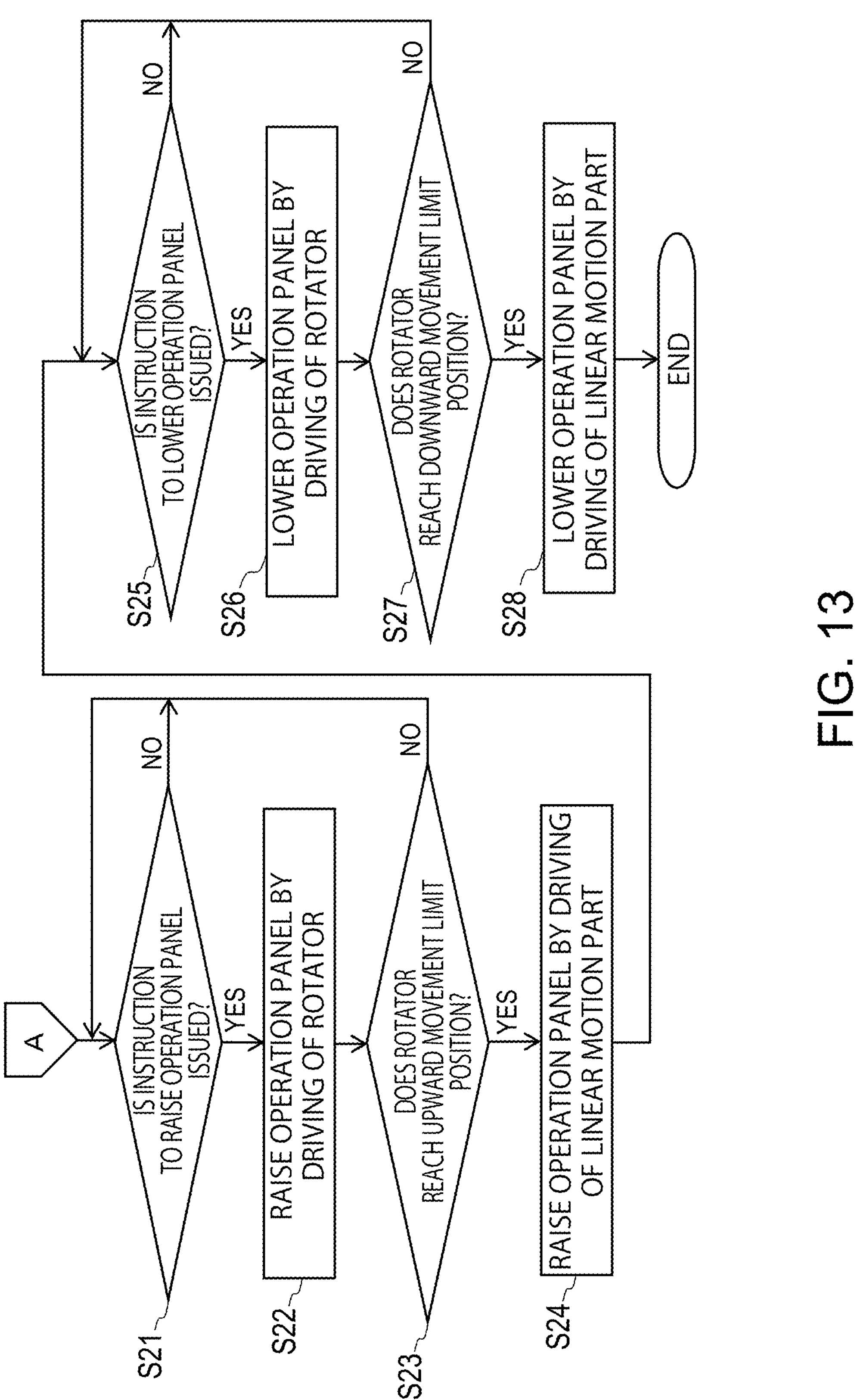
FIG. 13 is a subsequent flowchart of FIG. 12 and illustrates the operation of the ultrasonic diagnostic apparatus according to the modification of the second embodiment.

Next, an operation example of the ultrasonic diagnostic apparatus 1 according to the modification of the second embodiment configured as described above will be described. FIG. 12 is a flowchart illustrating the operation of the ultrasonic diagnostic apparatus 1 according to the modification of the second embodiment. FIG. 13 is a subsequent flowchart of FIG. 12 and illustrates the operation of the ultrasonic diagnostic apparatus 1 according to the modification of the second embodiment. It is noted that, in the initial state in FIG. 12, it is assumed that the operation panel 3 is not raised, and the linear motion part 91 and the rotator 71 are positioned at the respective downward movement limit positions.

Then, from the initial state, first, the driving control function 632 determines whether priority driving of the linear motion part 91 by the ON operation of the second designation switch SW-L is designated (step S19).

Here, first, an operation in a case where priority driving of the linear motion part 91 is designated will be described. After the priority driving of the linear motion part 91 is designated (step S19: YES), the driving control function 632 and the interlocking function 635 perform steps S11 to S15 as described in FIG. 9. Then, in step S15, when an instruction to lower the operation panel 3 is issued (step S15: YES), the driving control function 632 causes the second driver 10 to drive the linear motion part 91 so as to lower the operation panel 3 (step S111).

After the operation panel 3 is lowered, the interlocking function 635 determines whether the linear motion part 91 reaches the downward movement limit position (step S112).

When the linear motion part 91 reaches the downward movement limit position (step S112: YES), the interlocking function 635 causes the driving control function 632 to switch a control target from the driving of the linear motion part 91 to the driving of the rotator 71. Then, the driving control function 632 causes the first driver 8 to drive the rotator 71 in response to the operation of the switch SW, thereby further lowering the operation panel 3 (step S113). On the other hand, when the linear motion part 91 does not reach the downward movement limit position (step S112: NO), the driving control function 632 repeats the determination as to whether the instruction to lower the operation panel 3 is issued (step S15).

Next, an operation in a case where the priority driving of the linear motion part 91 is not designated will be described. When the priority driving of the linear motion part 91 is not designated (step S19: NO), the driving control function 632 determines whether the priority driving of the rotator 71 by the ON operation of the first designation switch SW-R is designated (step S110). When the priority driving of the rotator 71 is designated (step S110: YES), as illustrated in FIG. 13, the driving control function 632 determines whether an instruction to raise the operation panel 3 by the ON operation of the switch SW to the rising side is issued (step S21). On the other hand, when the priority driving of the rotator 71 is not designated (step S110: NO), the driving control function 632 repeats the determination as to whether the priority driving of the linear motion part 91 is designated, as illustrated in FIG. 12 (step S19).

When the instruction to raise the operation panel 3 is issued (step S21: YES), the driving control function 632 causes the first driver 8 to drive the rotator 71, thereby raising the operation panel 3 (step S22). On the other hand, when the instruction to raise the operation panel 3 is not issued (step S21: NO), the driving control function 632 repeats the determination as to whether the instruction to raise the operation panel 3 is issued (step S21).

After the operation panel 3 is raised, the interlocking function 635 determines whether the rotator 71 reaches the upward movement limit position (step S23).

When the rotator 71 reaches the upward movement limit position (step S23: YES), the interlocking function 635 causes the driving control function 632 to switch a control target from the driving of the rotator 71 to the driving of the linear motion part 91. Then, the driving control function 632 causes the second driver 10 to drive the linear motion part 91 in response to the fact that the ON operation of the switch SW to the rising side is continuously performed, thereby further raising the operation panel 3 (step S24). On the other hand, when the rotator 71 does not reach the upward movement limit position (step S23: NO), the driving control function 632 repeats the determination as to whether the instruction to raise the operation panel 3 is issued (step S21).

After rising of the operation panel 3 by the priority driving of the rotator 71 is completed, the driving control function 632 determines whether an instruction to lower the operation panel 3 by the ON operation of the switch SW to the falling side is issued (step S25).

When the instruction to lower the operation panel 3 is issued (step S25: YES), the driving control function 632 causes the first driver 8 to drive the rotator 71, thereby lowering the operation panel 3 (step S26). On the other hand, when the instruction to lower the operation panel 3 is not issued (step S25: NO), the driving control function 632 repeats the determination as to whether the instruction to lower the operation panel 3 is issued (step S25).

After the operation panel 3 is lowered, the interlocking function 635 determines whether the rotator 71 reaches the downward movement limit position (step S27).

When the rotator 71 reaches the downward movement limit position (step S27: YES), the interlocking function 635 causes the driving control function 632 to switch a control target from the driving of the rotator 71 to the driving of the linear motion part 91. Then, the driving control function 632 causes the second driver 10 to drive the linear motion part 91 in response to the continuous ON operation of the switch SW to the falling side, thereby further lowering the operation panel 3 (step S28). On the other hand, when the rotator 71 does not reach the downward movement limit position (step S27: NO), the driving control function 632 repeats the determination as to whether the instruction to lower the operation panel 3 is issued (step S25).

As described above, in the modification of the second embodiment, the drivers 8 and 10 preferentially drive one of the rotator 71 and the linear motion part 91 designated by the ON operation of the designation switches SW-R and SW-L. When one of the rotator 71 and the linear motion part 91 that has been preferentially driven reaches the movement limit, the drivers 8 and 10 drive the other of the rotator 71 and the linear motion part 91.

As a result, a degree of freedom in adjusting the height of the operation panel 3 can be improved.

Third Embodiment

Figure 14:
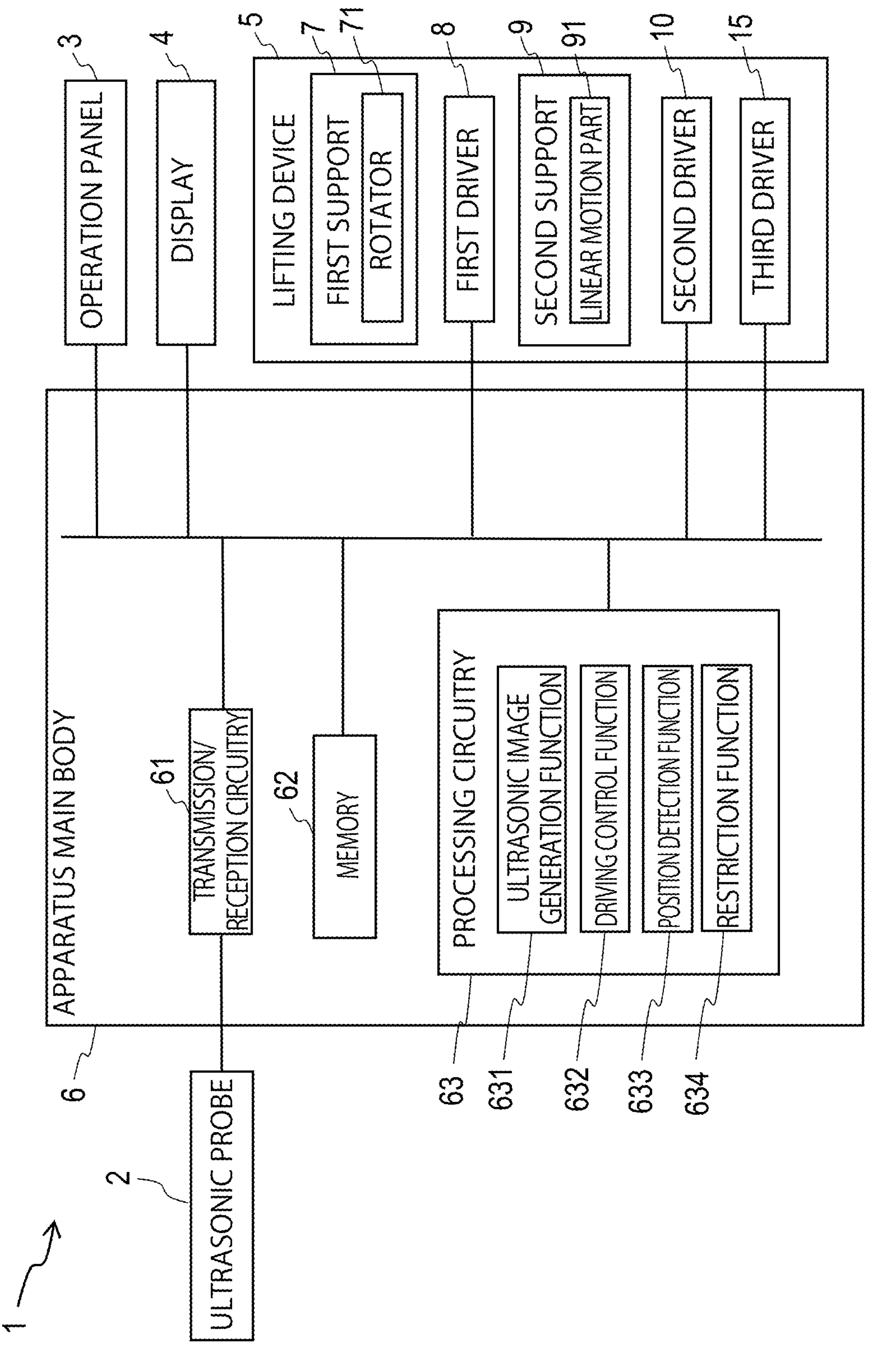
FIG. 14 is a block diagram illustrating a configuration example of an ultrasonic diagnostic apparatus according to a third embodiment.
Figure 15A:
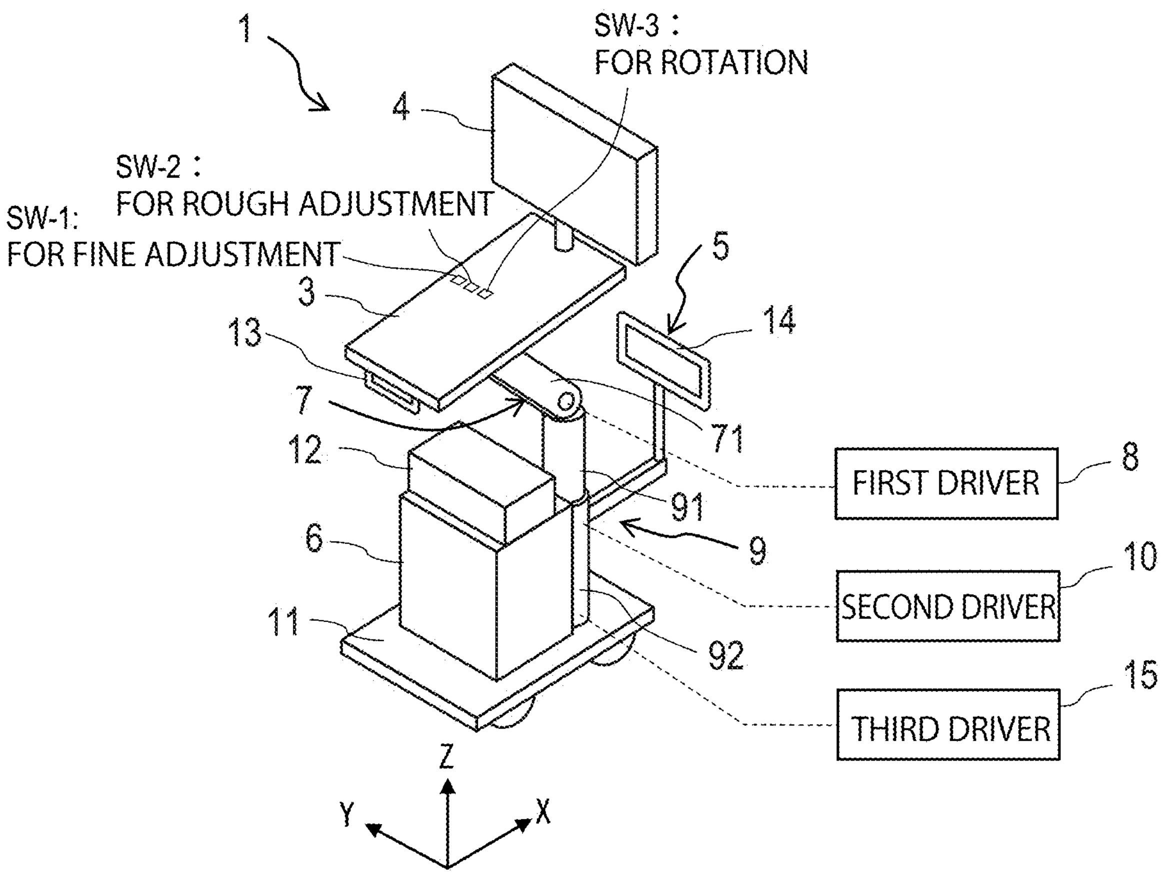
FIG. 15A is a perspective view illustrating the configuration example of the ultrasonic diagnostic apparatus according to the third embodiment.
Figure 15B:
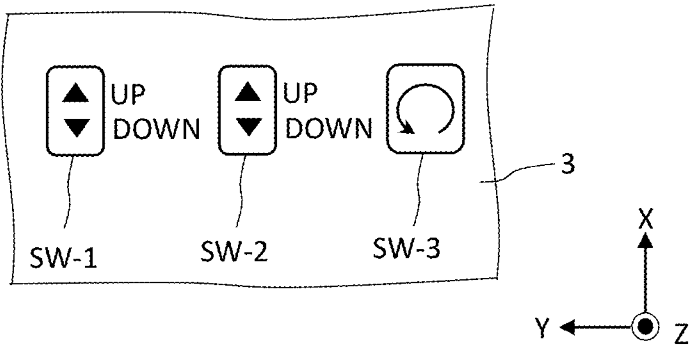
FIG. 15B is a plan view illustrating a configuration example of an operation panel of the ultrasonic diagnostic apparatus according to the third embodiment.

Next, a third embodiment in which the second support 9 is rotated will be described, focusing on a difference between the third embodiment and the first embodiment. FIG. 14 is a block diagram illustrating a configuration example of an ultrasonic diagnostic apparatus 1 according to the third embodiment. FIG. 15A is a perspective view illustrating the configuration example of the ultrasonic diagnostic apparatus 1 according to the third embodiment. FIG. 15B is a plan view illustrating a configuration example of an operation panel of the ultrasonic diagnostic apparatus 1 according to the third embodiment.

In the third embodiment, the second support 9 is rotatable around a rotation axis in the linear motion direction of the linear motion part 91. As illustrated in FIG. 14, the lifting device 5 of the ultrasonic diagnostic apparatus 1 according to the third embodiment further includes a third driver 15 in addition to the configuration of the first embodiment. The third driver 15 drives the second support 9 to rotate the second support 9 around the rotation axis in the linear motion direction of the linear motion part 91. The third driver 15 includes, for example, a motor, a driving force transmission member such as a gear that transmits driving force of the motor to the linear motion support 92 of the second support 9, and a driving circuitry of the motor. In the third embodiment, the position detection function 633 detects the position of the second support 9 in the rotation direction in addition to detecting the position of the second support 9 in the linear motion direction (that is, in the height direction) as described in the first embodiment and the second embodiment. Similarly to the position of the second support 9 in the linear motion direction, the position of the second support 9 in the rotation direction may be detected using a driving amount of the second support 9 by the third driver 15, such as a rotation amount of the motor, or a sensor such as an optical sensor. A detection result of the position of the second support 9 in the rotation direction by the position detection function 633 is used to limit the rotation range of the rotator 71 by the restriction function 634.

As illustrated in FIGS. 15A and 15B, the operation panel 3 of the ultrasonic diagnostic apparatus 1 according to the third embodiment further includes a third switch SW3 that instructs rotation of the second support 9, in addition to the configuration of the first embodiment. In the example illustrated in FIG. 15A, the third driver 15 generates driving force when the third switch SW3 is turned on. By rotating the second support 9, the operation panel 3 can be horizontally shifted from the apparatus main body 6.

The operation panel 3 is horizontally shifted from the apparatus main body 6 by the rotation of the second support 9, and then, is movable below the upper end of the apparatus main body 6 by the rotation of the rotator 71.

Figure 16:
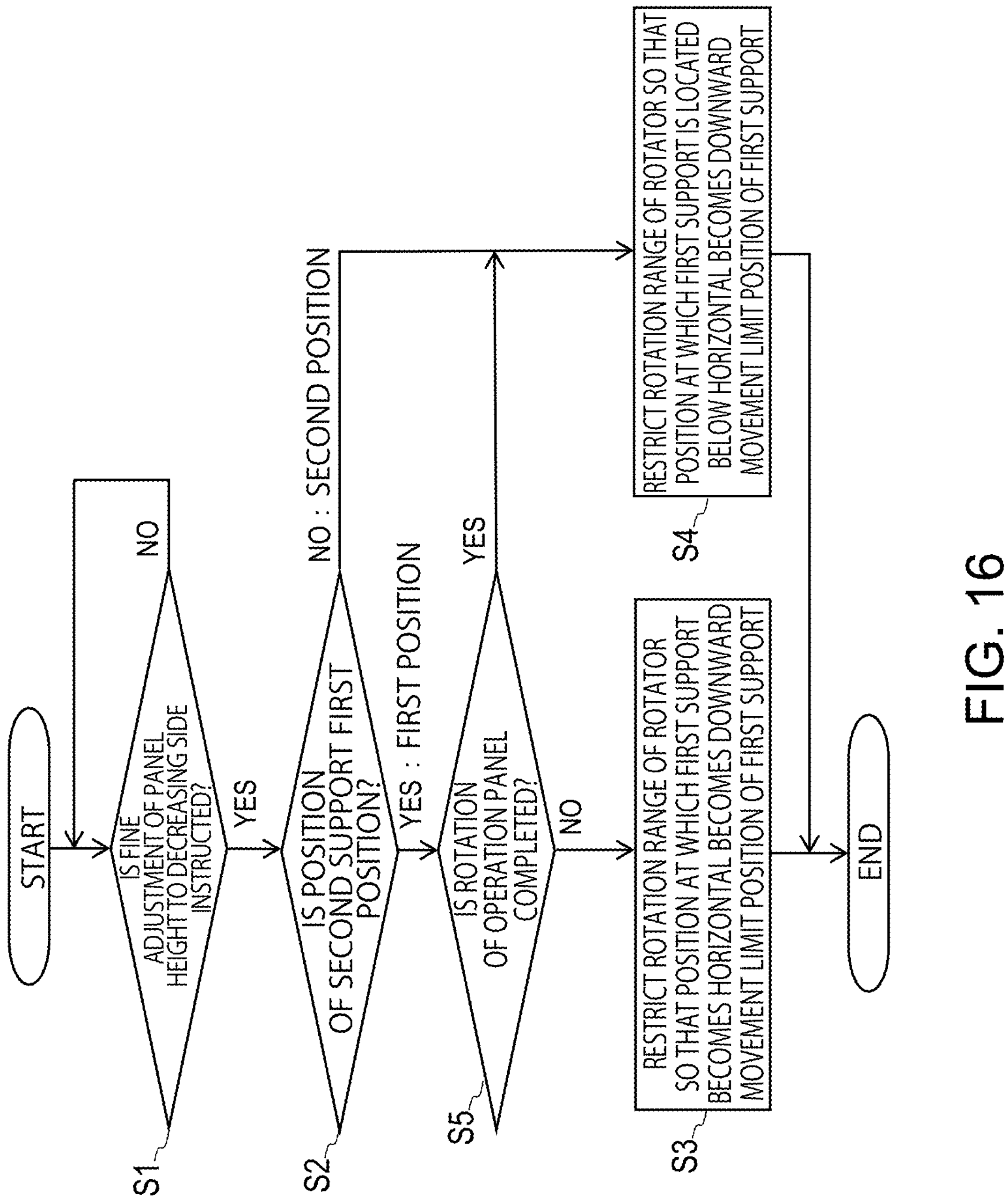
FIG. 16 is a flowchart illustrating an operation example of the ultrasonic diagnostic apparatus according to the third embodiment.
Figure 17:
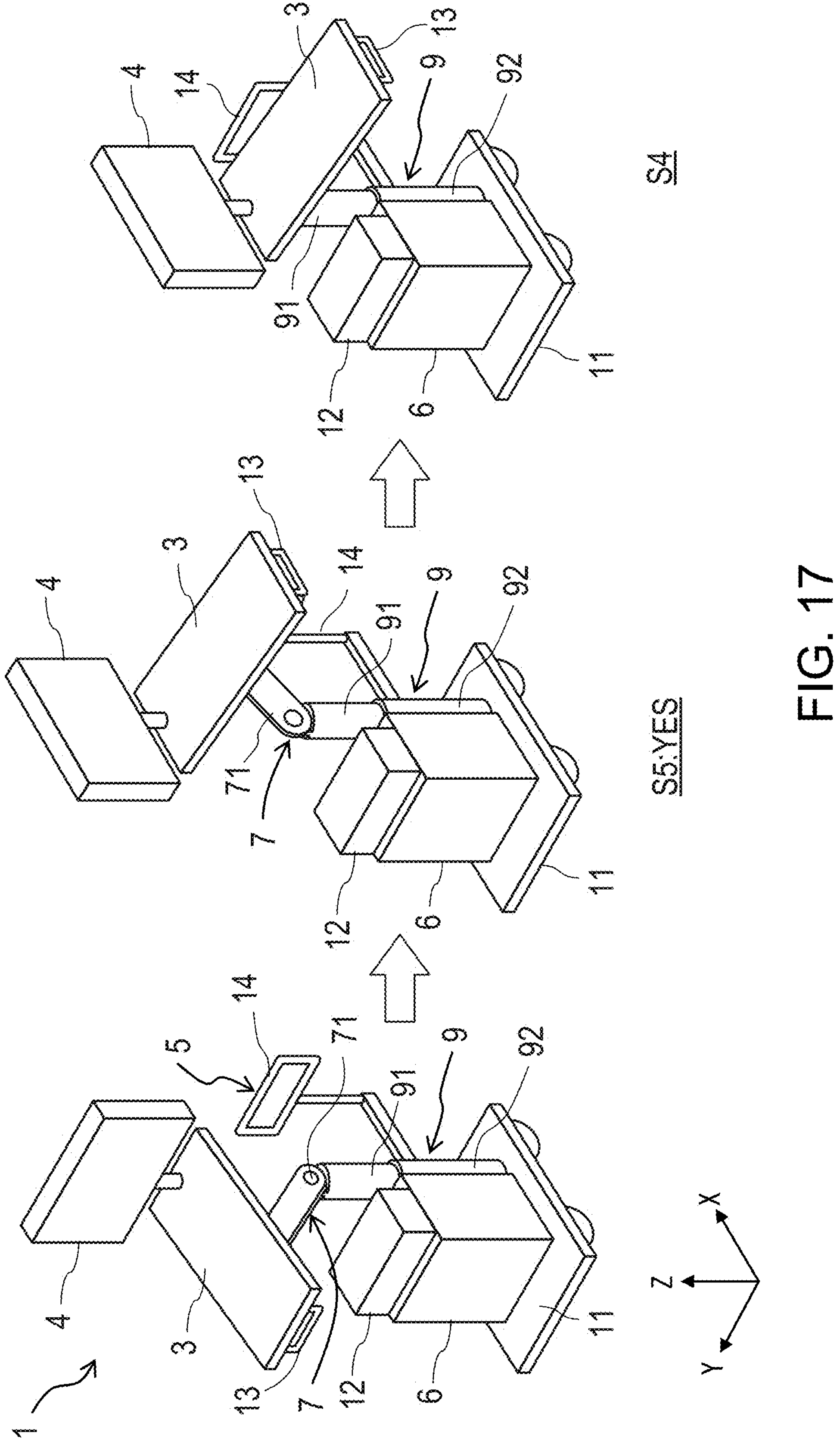
FIG. 17 is a perspective view illustrating the operation example of the ultrasonic diagnostic apparatus according to the third embodiment.

FIG. 16 is a flowchart illustrating an operation example of the ultrasonic diagnostic apparatus 1 according to the third embodiment. FIG. 17 is a perspective view illustrating the operation example of the ultrasonic diagnostic apparatus 1 according to the third embodiment. For example, as illustrated in FIG. 16, even in a case where the position of the second support 9 is the first position, when it is determined that the operation panel 3 is rotated by the third driver 15 based on a detection result of the position of the second support 9 in the rotation direction by the position detection function 633 (step S5: YES), the restriction function 634 restricts the rotation range of the rotator 71 so as to allow the first support 7 to be located below the horizontal at the downward movement limit position (step S4). As a result, as illustrated in FIG. 17, the operation panel 3 can be made lower than the upper end of the apparatus main body 6 at the downward movement limit position.

As described above, in the third embodiment, the second support 9 is rotatable around the rotation axis in the linear motion direction. The operation panel 3 is horizontally shifted from the apparatus main body 6 by the rotation of the second support 9, and then is movable below the upper end of the apparatus main body 6 by the rotation of the rotator 71.

As a result, a degree of freedom in adjusting the height of the operation panel 3 can be improved.

Fourth Embodiment

Figure 18:
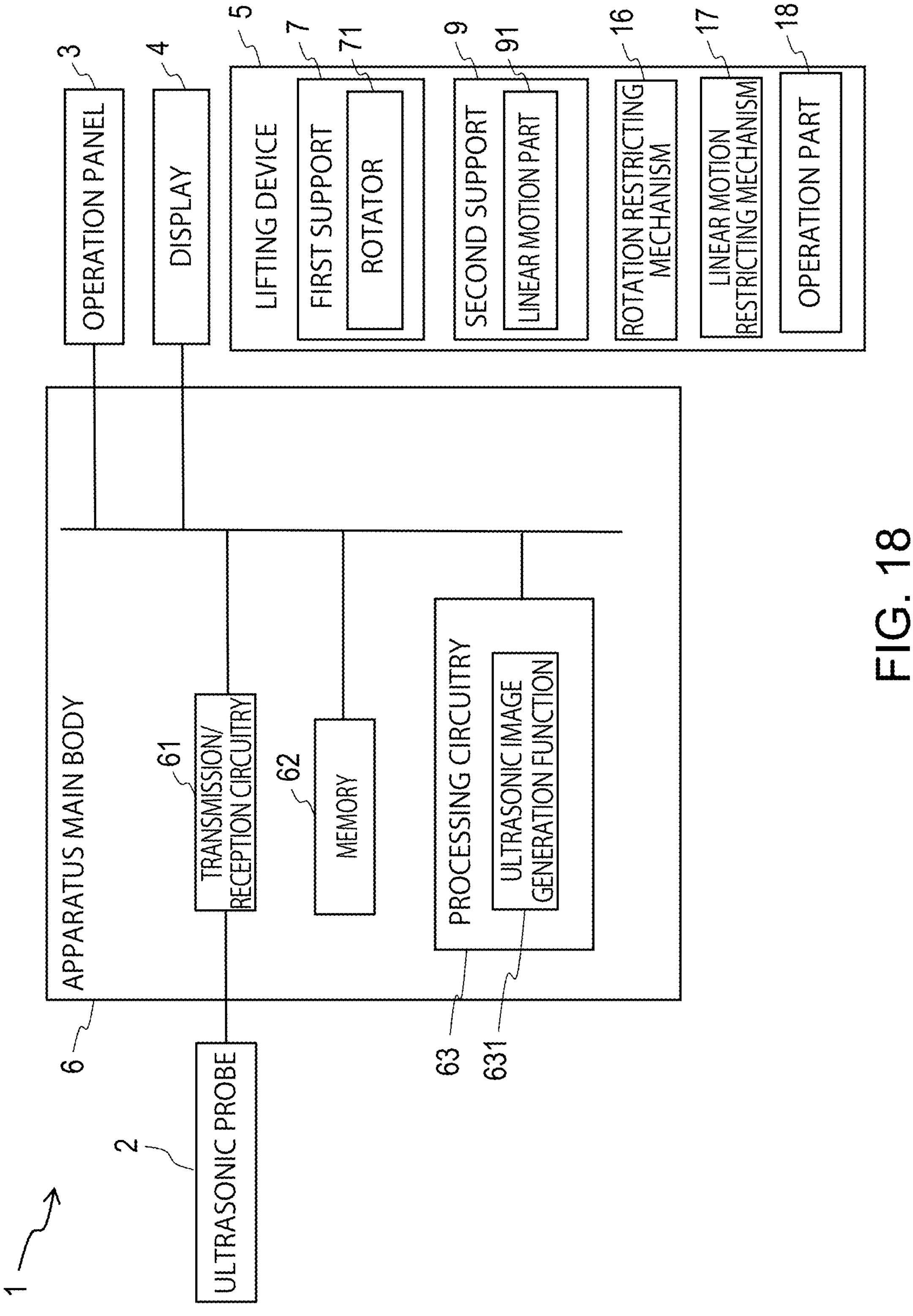
FIG. 18 is a block diagram illustrating a configuration example of an ultrasonic diagnostic apparatus according to a fourth embodiment.

Next, a fourth embodiment in which the height of the operation panel 3 is manually adjusted will be described, focusing on a difference between the fourth embodiment and the first embodiment. FIG. 18 is a block diagram illustrating a configuration example of the ultrasonic diagnostic apparatus 1 according to the fourth embodiment.

An example in which the height of the operation panel 3 is electrically adjusted has been described above. On the other hand, the ultrasonic diagnostic apparatus 1 according to the fourth embodiment is configured to manually adjust the height of the operation panel 3.

Specifically, as illustrated in FIG. 18, the lifting device 5 in the fourth embodiment does not include the first driver 8 and the second driver 10. That is, in the fourth embodiment, the rotation of the rotator 71 and the linear motion of the linear motion part 91 are manually performed by a user. The lifting device 5 according to the fourth embodiment includes a rotation restricting mechanism 16, a linear motion restricting mechanism 17, and an operation part 18. The rotation restricting mechanism 16 is an example of a first restrictor. The linear motion restricting mechanism 17 is an example of a second restrictor.

The rotation restricting mechanism 16 restricts the rotation of the rotator 71. The linear motion restricting mechanism 17 restricts the linear motion of the linear motion part 91. The operation part 18 is provided at the front handle 13 provided on the operation panel 3. The front handle 13 is an example of a grip portion. The operation part 18 performs an operation of releasing either restriction of the rotation of the rotator 71 by the rotation restricting mechanism 16 or restriction of the linear motion of the linear motion part 91 by the linear motion restricting mechanism 17 depending on a gripping position of the front handle 13.

Figure 19:
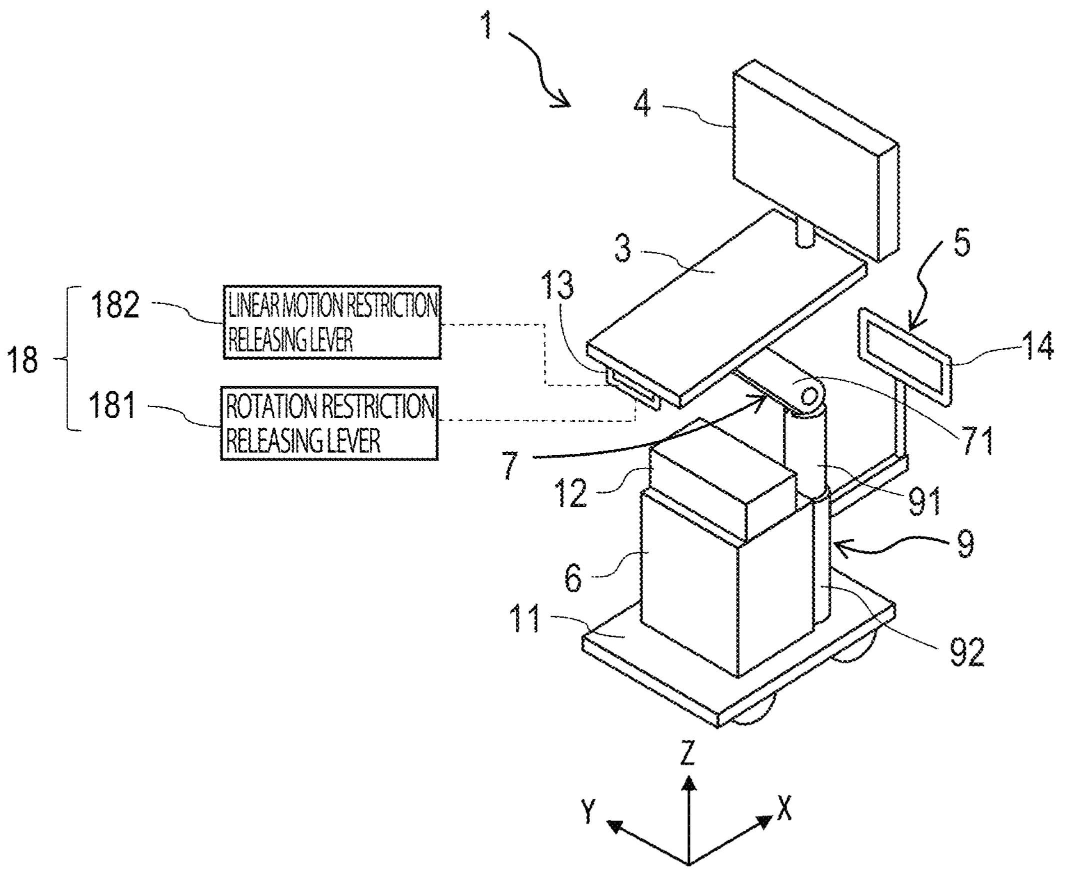
FIG. 19 is a perspective view illustrating the configuration example of the ultrasonic diagnostic apparatus according to the fourth embodiment.

FIG. 19 is a perspective view illustrating a configuration example of the ultrasonic diagnostic apparatus 1 according to the fourth embodiment. In the example illustrated in FIG. 19, the operation part 18 includes a rotation restriction releasing lever 181 and a linear motion restriction releasing lever 182. The rotation restriction releasing lever 181 is provided at a central portion of the front handle 13. The rotation restriction releasing lever 181 is operated when the user grips the central portion of the front handle 13, and releases the restriction of the rotation of the rotator 71 by the rotation restricting mechanism 16. The linear motion restriction releasing lever 182 is provided at a side portion of the front handle 13. The linear motion restriction releasing lever 182 is operated when the user grips the side portion of the front handle 13, and releases the restriction of the linear motion of the linear motion part 91 by the linear motion restricting mechanism 17. The linear motion restriction releasing lever 182 may be provided at both side portions (that is, opposite sides) of the front handle 13.

Figure 20:
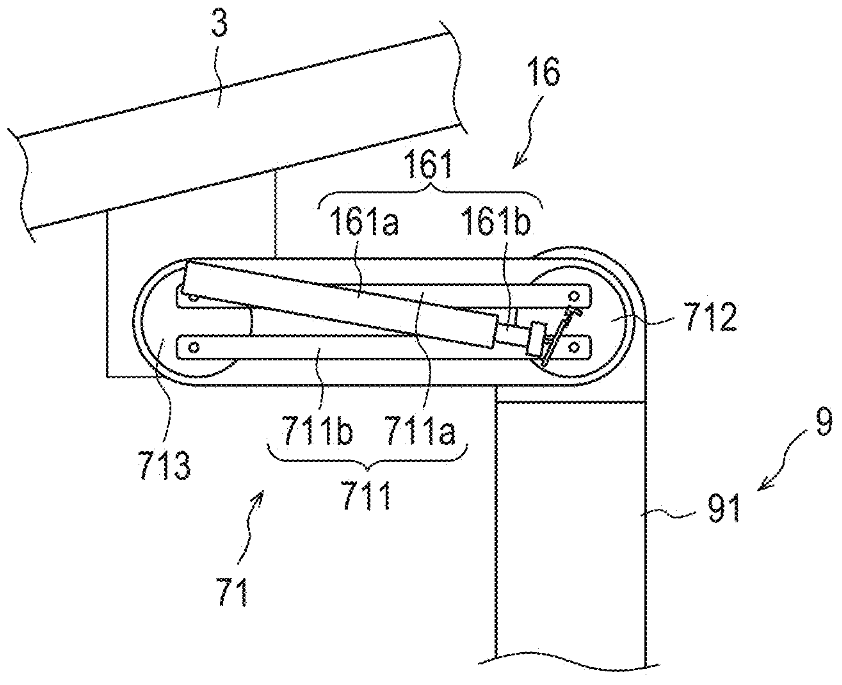
FIG. 20 is a diagram illustrating a configuration example of a rotator and a rotation restricting mechanism of the ultrasonic diagnostic apparatus according to the fourth embodiment.

FIG. 20 is a diagram illustrating a configuration example of the rotator 71 and the rotation restricting mechanism 16 of the ultrasonic diagnostic apparatus 1 according to the fourth embodiment. In the example illustrated in FIG. 20, the rotator 71 includes a parallel link 711, a rotation support 712, and a panel connection portion 713. The parallel link 711 extends from one end on the second support 9 side toward the other end on the operation panel 3 side, and is rotatable around one end on the second support 9 side. The rotation support 712 rotatably supports one end of the parallel link 711. The panel connection portion 713 connects the parallel link 711 to the operation panel 3.

More specifically, the parallel link 711 has an upper link 711*a* and a lower link 711*b* arranged in parallel with each other at an interval in the vertical direction. The upper link 711*a* and the lower link 711*b* extend from one end on the second support 9 side toward the other end on the operation panel 3 side. One end of the upper link 711*a* is rotatably supported by a first fulcrum of the rotation support 712. One end of the lower link 711*b* is rotatably supported by a second fulcrum of the rotation support 712. The other end of the upper link 711*a* is rotatably connected to the panel connection portion 713. The other end of the lower link 711*b* is also rotatably connected to the panel connection portion 713. The operation panel 3 is connected to the panel connection portion 713.

Figure 21:
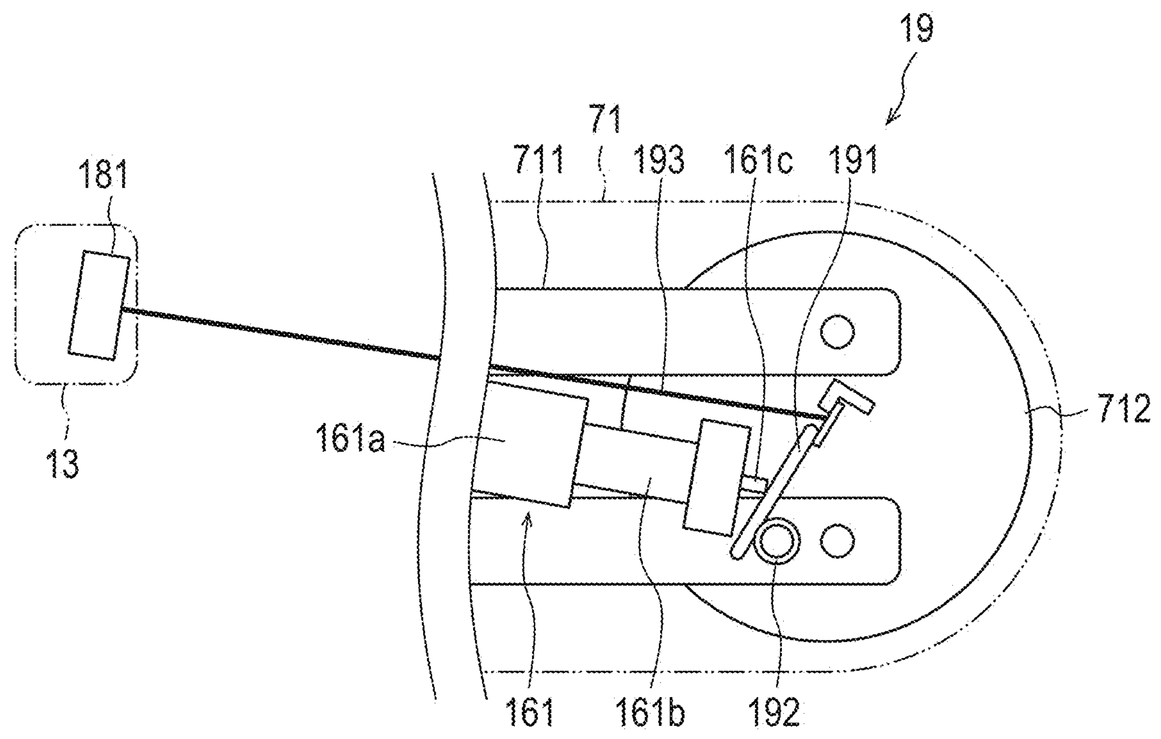
FIG. 21 is an enlarged view illustrating a configuration example of an operation part of the ultrasonic diagnostic apparatus according to the fourth embodiment.

FIG. 21 is an enlarged view illustrating a configuration example of the operation part 18 of the ultrasonic diagnostic apparatus 1 according to the fourth embodiment. In the example illustrated in FIGS. 20 and 21, the rotation restricting mechanism 16 includes a gas spring 161. The gas spring 161 includes a cylindrical cylinder 161*a*, a disk-shaped piston (not illustrated) inserted into the cylinder 161*a*, a rod-shaped piston rod 161*b* connected to the piston, and a push rod 161*c* protruding from the piston rod 161*b*.

The gas spring 161 is fixed to the rotator 71 so that the length of the gas spring 161 changes depending on a rotation amount of the rotator 71. A part of the piston rod 161*b* is exposed from the cylinder 161*a*. The length of the piston rod 161*b* exposed from the cylinder 161*a* changes as the parallel link 711 is deformed in accordance with the rotation of the rotator 71. The gas spring 161 is filled with gas and oil. A region in which the gas spring 161 is filled with oil is partitioned by a piston in which an orifice (that is, a hole through which oil passes) is formed. The push rod 161*c* is connected to a valve that opens and closes the orifice. When the push rod 161*c* is not pushed in, the orifice is closed by the valve. When the orifice is closed, a flow of oil between the regions partitioned by the piston is stopped, and movement of the piston is stopped. When movement of the piston is stopped, the length of the gas spring 161 is fixed. By fixing the length of the gas spring 161, the rotation of the parallel link 711 is prohibited. When the rotation of the parallel link 711 is prohibited, the rotation of the rotator 71 is prohibited. That is, when the push rod 161*c* is not pushed in, the rotator 71 is in a locked state in which rotation is prohibited.

On the other hand, when the push rod 161*c* is pushed in, the orifice is opened by the valve. By opening the orifice, oil in the region partitioned by the piston can pass through the orifice, and the piston becomes movable. When the piston is movable, the length of the gas spring 161 is variable. Since the length of the gas spring 161 is variable, the rotation of the parallel link 711 is permitted. When the rotation of the parallel link 711 is permitted, the rotation of the rotator 71 is permitted. That is, when the push rod 161*c* is pushed in, the rotator 71 is in a released state in which the prohibition of rotation is released. In the released state, the rotator 71 can move the operation panel 3 upwards and downwards in response to a manual operation of the user.

Further, in the example illustrated in FIG. 21, the ultrasonic diagnostic apparatus 1 further includes a lock releasing mechanism 19 that releases the prohibition of rotation of the rotator 71 in conjunction with the rotation restriction releasing lever 181. The lock releasing mechanism 19 includes a lock releasing plate 191, a lock releasing plate fulcrum 192, and a wire 193.

The lock releasing plate 191 is disposed so as to be in contact with the push rod 161*c*. The lock releasing plate 191 is pressed in a direction away from the push rod 161*c* by an elastic member (not illustrated) such as a spring. One end of the lock releasing plate 191 is rotatably supported by the lock releasing plate fulcrum 192. One end of the wire 193 is fixed to the other end (that is, the end on the opposite side of the lock releasing plate fulcrum 192) of the lock releasing plate 191. The other end of the wire 193 is fixed to the rotation restriction releasing lever 181.

Figure 22:
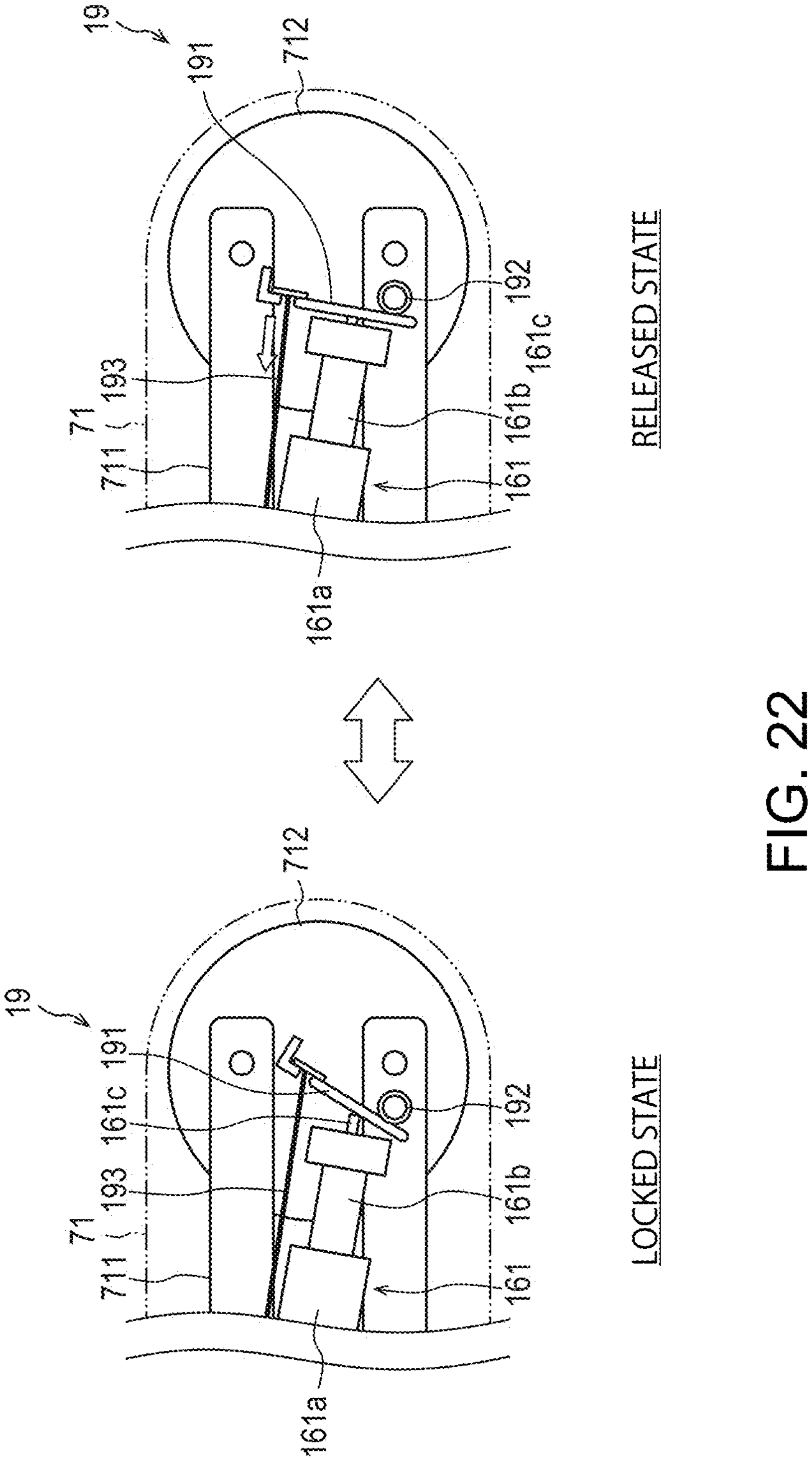
FIG. 22 is a diagram illustrating an operation example of the rotation restricting mechanism of the ultrasonic diagnostic apparatus according to the fourth embodiment.
Figure 23:
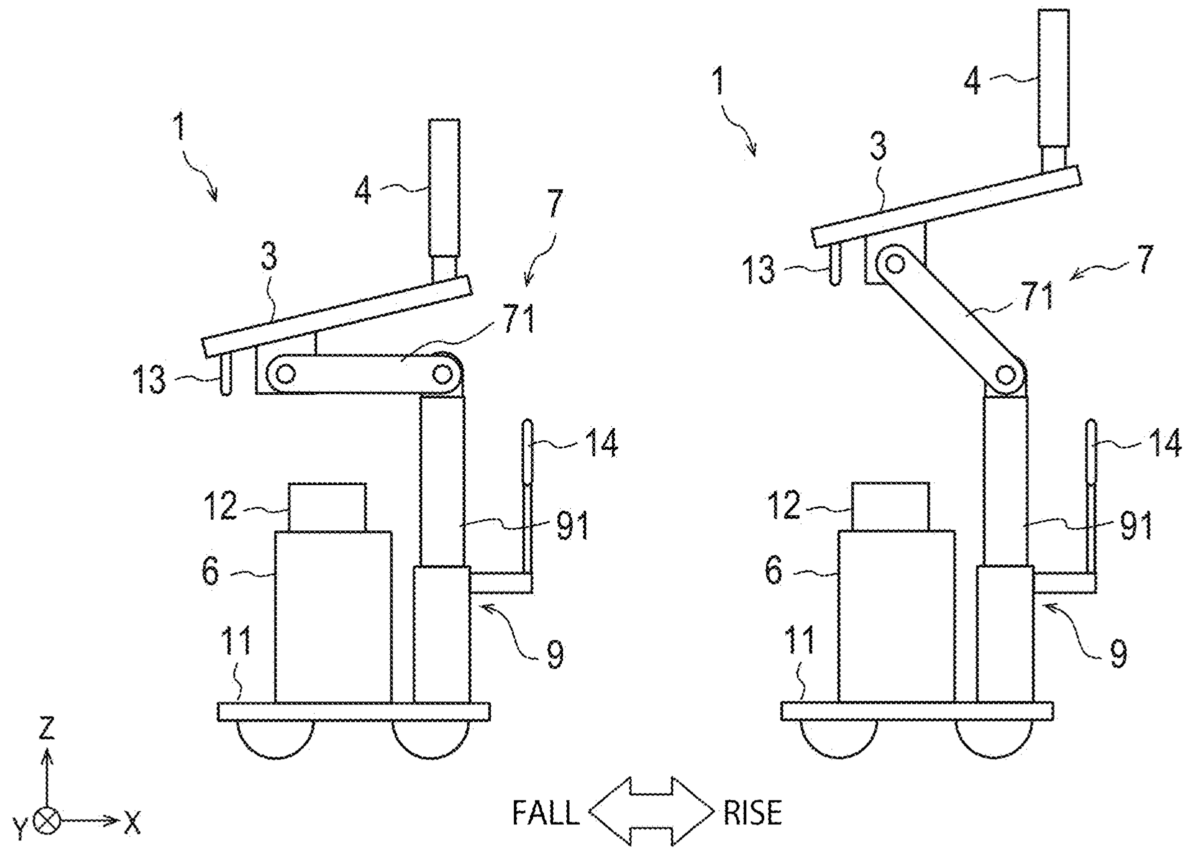
FIG. 23 is a side view illustrating an operation example of the ultrasonic diagnostic apparatus according to the fourth embodiment.
Figure 24:
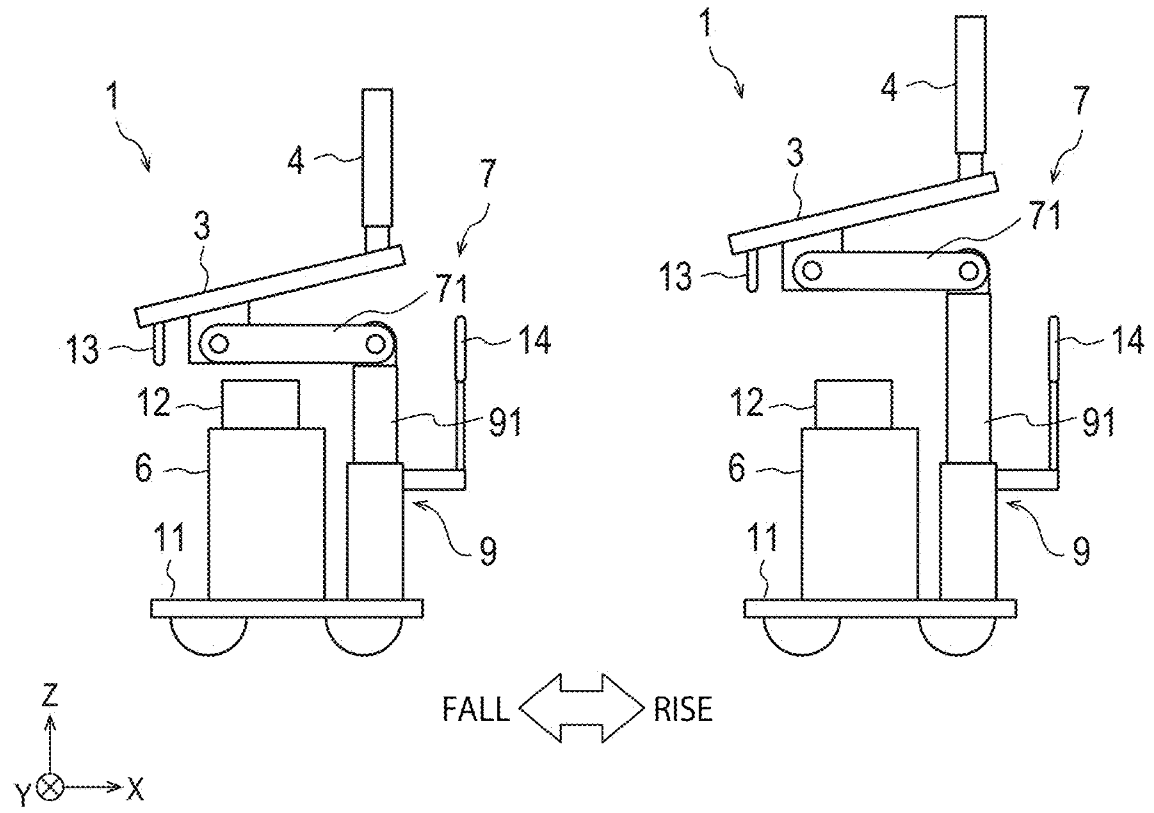
FIG. 24 is a side view illustrating another operation example of the ultrasonic diagnostic apparatus according to the fourth embodiment.

Next, an operation example of the ultrasonic diagnostic apparatus 1 according to a modification of the fourth embodiment configured as described above will be described. FIG. 22 is a diagram illustrating an operation example of the rotation restricting mechanism 16 of the ultrasonic diagnostic apparatus 1 according to the fourth embodiment. FIG. 23 is a side view illustrating an operation example of the ultrasonic diagnostic apparatus 1 according to the fourth embodiment. FIG. 24 is a side view illustrating another operation example of the ultrasonic diagnostic apparatus 1 according to the fourth embodiment.

When the central portion of the front handle 13 is gripped by the user, the rotation restriction releasing lever 181 is operated. When the rotation restriction releasing lever 181 is operated, the wire 193 is pulled toward the rotation restriction releasing lever 181. When the wire 193 is pulled toward the rotation restriction releasing lever 181, the lock releasing plate 191 fixed to the wire 193 rotates in a direction of pushing the push rod 161*c*. When the lock releasing plate 191 rotates in the direction of pushing the push rod 161*c*, the push rod 161*c* is pushed in. When the push rod 161*c* is pushed in, the length of the gas spring 161 becomes variable, and the rotation of the rotator 71 is permitted. Therefore, by gripping the central portion of the front handle 13, as illustrated in FIG. 22, the rotator 71 can be switched from a locked state to a released state, and the rotator 71 can be rotated by manual operation. As a result, as illustrated in FIG. 23, the height of the operation panel 3 can be finely adjusted by vertically moving the operation panel 3 while rotating the operation panel 3.

On the other hand, when the central portion of the front handle 13 is not gripped by the user, the rotation restriction releasing lever 181 is not operated, and the wire 193 is not pulled. Since the wire 193 is not pulled, the lock releasing plate 191 is not rotated, and the push rod 161*c* is not pushed in. Therefore, when the central portion of the front handle 13 is not gripped, the rotator 71 is in the locked state, and fine adjustment of the height of the operation panel 3 is prohibited.

Similarly to the rotation restricting mechanism 16, the linear motion restricting mechanism 17 may include a gas spring. Further, the ultrasonic diagnostic apparatus 1 may further include a lock releasing mechanism (that is, a lock releasing plate, a lock releasing plate fulcrum, and a wire) that interlocks with the linear motion restriction releasing lever 182. The cylinder of the gas spring may be fixed to the linear motion support 92, and the piston rod of the gas spring may be fixed to the linear motion part 91. In such a configuration, when the side portion of the front handle 13 is gripped by the user, the linear motion restriction releasing lever 182 is operated. When the linear motion restriction releasing lever 182 is operated, the wire having one end fixed to the linear motion restriction releasing lever 182 is pulled toward the linear motion restriction releasing lever 182. When the wire is pulled toward the linear motion restriction releasing lever 182, the lock releasing plate fixed to the other end of the wire rotates around the lock releasing plate fulcrum in a direction of pushing the push rod. When the lock releasing plate rotates in the direction of pushing the push rod, the push rod is pushed in. When the push rod is pushed in, the length of the gas spring becomes variable, and the linear motion of the linear motion part 91 is permitted. Therefore, by gripping the side portion of the front handle 13, the linear motion part 91 is switched from the locked state to the released state, and the linear motion part 91 can be linearly moved by manual operation. As a result, as illustrated in FIG. 24, the height of the operation panel 3 can be roughly adjusted by moving the linear motion part 91 upwards and downwards. On the other hand, when the side portion of the front handle 13 is not gripped, the linear motion restriction releasing lever 182 is not operated, and the push rod is not pushed in. Therefore, when the side portion of the front handle 13 is not gripped, the linear motion part 91 is in the locked state, and rough adjustment of the height of the operation panel 3 is prohibited.

As described above, in the fourth embodiment, the rotation restricting mechanism 16 restricts the rotation of the rotator 71. Further, the linear motion restricting mechanism 17 restricts the linear motion of the linear motion part 91. In addition, the operation part 18 provided at the front handle 13 performs an operation of releasing either the restriction of the rotation of the rotator 71 by the rotation restricting mechanism 16 or the restriction of the linear motion of the linear motion part 91 by the linear motion restricting mechanism 17 depending on the gripping position of the front handle 13.

As a result, since power is not required to adjust the height of the operation part 18, power consumption of the ultrasonic diagnostic apparatus 1 can be reduced.

Modification of Fourth Embodiment

Figure 25:
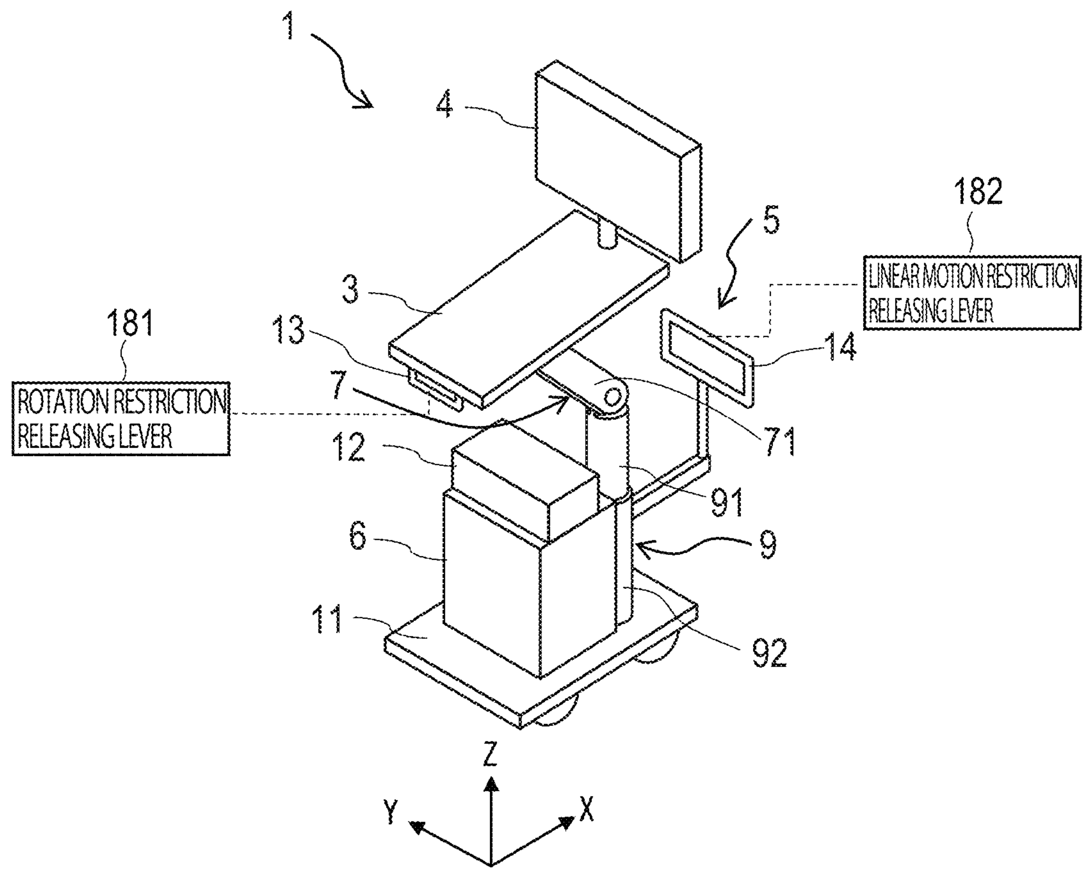
FIG. 25 is a perspective view illustrating an ultrasonic diagnostic apparatus according to a modification of the fourth embodiment.

Next, a modification in which the lock of the linear motion part 91 is released according to the gripping of the rear handle 14 will be described. FIG. 25 is a perspective view illustrating an ultrasonic diagnostic apparatus 1 according to the modification of the fourth embodiment. As illustrated in FIG. 25, the linear motion restriction releasing lever 182 (i.e., a second operation part) may be provided at the rear handle 14 instead of the front handle 13. The rear handle 14 is an example of the second grip portion. According to the example illustrated in FIG. 25, the user can release the restriction of the linear motion of the linear motion part 91 by the linear motion restricting mechanism 17 (i.e., a third restrictor) by gripping the rear handle 14. Therefore, the user can roughly adjust the height of the operation panel 3 while gripping the rear handle 14. Such a configuration is suitable, for example, when the panel height is finely adjusted by the rotator 71 in normal use, and the panel height is roughly adjusted by the linear motion part 91 in limited cases such as installation and movement of the ultrasonic diagnostic apparatus 1. In addition, according to the modification of the fourth embodiment, it is not necessary to release the restriction of the linear motion part 91 by the linear motion restriction releasing lever 182 provided at the front handle 13 illustrated in FIG. 19 so as to lower the height of the linear motion part 91, and then to turn to the rear side of the ultrasonic diagnostic apparatus 1 so as to move the ultrasonic diagnostic apparatus 1 by holding the rear handle 14, so that ease of movement of the ultrasonic diagnostic apparatus 1 can be improved.

It is noted that the mechanism (that is, the rotation restricting mechanism 16, the linear motion restricting mechanism 17, the operation part 18, and the lock releasing mechanism 19) for adjusting the height of the operation panel 3 by manual operation described in the fourth embodiment can also be applied instead of the drivers 8, 10, and 15 in order to realize the operation example of the lifting device 5 described in the first to third embodiments.

It is noted that the term "processor" used in the above description means, for example, a central processing unit (CPU), a graphics processing unit (GPU), or circuitry such as an application specific integrated circuit (ASIC), a programmable logic device (for example, a simple programmable logic device (SPLD), a complex programmable logic device (CPLD), and a field programmable gate array (FPGA). The processor implements a function thereof by reading and executing a program stored in a memory. It is noted that, instead of storing the program in the memory, the program may be directly incorporated in a circuitry of the processor. In this case, the processor implements a function thereof by reading and executing the program incorporated in the circuitry. It is noted that the processor is not limited to a case of being configured as a single processor circuitry, and a plurality of independent circuitry may be combined to be configured as one processor to implement the function. Furthermore, a plurality of components in FIG. 1 may be integrated into one processor to implement the function.

According to at least one embodiment described above, the height adjustment range of the operation panel can be expanded, the amount of movement of the operation panel in the depth direction can be reduced, and the depth dimension of the ultrasonic diagnostic apparatus can be reduced.

Although several embodiments have been described above, these embodiments have been presented only as examples, and are not intended to limit the scope of the invention. The novel devices and methods described herein can be implemented in a variety of other forms. In addition, various omissions, substitutions, and changes can be made to the forms of the device and the method described in the present specification without departing from the gist of the invention. The appended claims and equivalents thereto are intended to include such forms and modifications as fall within the scope and spirit of the invention.

What is claimed is:

1. An ultrasonic diagnostic apparatus, comprising:
- an operation panel configured to receive an operation of a user;
- a first support configured to support the operation panel so as to allow a height of the operation panel to be changed;
- a second support configured to support the first support so as to allow the height of the operation panel to be changed;
- a linear motion part configured to linearly move the second support in a vertical direction; and
- a rotator provided at a position along a moving direction of the second support,
- wherein the second support is connected to the first support via the rotator, and the first support is rotated about a rotational axis of the rotator.

2. The ultrasonic diagnostic apparatus according to claim 1, further comprising processing circuitry configured to restrict a rotation range of the rotator depending on a height of the second support linearly moved by the linear motion part.

3. The ultrasonic diagnostic apparatus according to claim 2, wherein the processing circuitry is configured to restrict, when a position of the second support in a linear motion direction is a first position, the rotation range of the rotator so that the first support becomes horizontal.

4. The ultrasonic diagnostic apparatus according to claim 3, wherein the processing circuitry is configured to restrict, when the position of the second support in the linear motion direction is a second position higher than the first position, the rotation range of the rotator so as to allow the first support to be located below the horizontal.

5. The ultrasonic diagnostic apparatus according to claim 1, wherein the rotator and the linear motion part are independently operable.

6. The ultrasonic diagnostic apparatus according to claim 1, wherein the rotator and the linear motion part are interlockable with each other.

7. The ultrasonic diagnostic apparatus according to claim 1, wherein the second support is rotatable around a rotation axis in a linear motion direction, and the operation panel is movable, after being horizontally shifted from an apparatus main body by rotation of the second support, below an upper end of the apparatus main body by rotation of the rotator.

8. The ultrasonic diagnostic apparatus according to claim 1, further comprising:
- a first restrictor configured to restrict rotation of the rotator;
- a second restrictor configured to restrict linear motion of the linear motion part;
- a grip portion provided on the operation panel; and
- an operation part provided at the grip portion and configured to perform, depending on a grip position of the grip portion, an operation of releasing either restriction of the rotation of the rotator by the first restrictor or restriction of the linear motion of the linear motion part by the second restrictor.

9. The ultrasonic diagnostic apparatus according to claim 1, further comprising:
- a third restrictor configured to restrict linear motion of the linear motion part;
- a second grip portion provided at the second support; and
- a second operation part provided at the second grip portion and configured to perform, depending on gripping of the second grip portion, an operation of releasing restriction of the linear motion of the linear motion part by the third restrictor.

10. The ultrasonic diagnostic apparatus according to claim 2, wherein the processing circuitry is configured to electrically restrict the rotation range of the rotator.

11. The ultrasonic diagnostic apparatus according to claim 1, further comprising a driver configured to electrically drive the rotator and the linear motion part.

12. The ultrasonic diagnostic apparatus according to claim 11, wherein the driver is configured to drive, when one of the rotator and the linear motion part reaches a movement limit, the other of the rotator and the linear motion part.

13. The ultrasonic diagnostic apparatus according to claim 12, wherein
- the rotator and the linear motion part are configured to be interlockable with each other, and
- the ultrasonic diagnostic apparatus further comprises a third operation part configured to perform an operation of designating which of the rotator and the linear motion part is to be preferentially driven.

14. The ultrasonic diagnostic apparatus according to claim 13, wherein the third operation part is provided on the operation panel.

15. The ultrasonic diagnostic apparatus according to claim 3, wherein the first position is a position of the second support, wherein the position of the second support allows a distance between the first support and a structure below the first support to become a threshold distance or less when the first support becomes horizontal at the first position.

16. The ultrasonic diagnostic apparatus according to claim 15, wherein the second position is a position of the second support, wherein the position of the second support allows the first support to be rotatable up to a position lower than the horizontal without contacting the structure below the first support at the second position.

17. The ultrasonic diagnostic apparatus according to claim 16, wherein the processing circuitry is configured to restrict, when the position of the second support in the linear motion direction is the second position, the rotation range of the rotator so as to allow the first support to be rotatable up to the position lower than the horizontal without contacting the structure below the first support.

18. The ultrasonic diagnostic apparatus according to claim 7, wherein the processing circuitry is configured to restrict, when a position of the second support in the linear motion direction is a first position, a rotation range of the rotator so as to allow the operation panel to move below an upper end of the apparatus main body when the operation panel is horizontally shifted from the apparatus main body by the rotation of the second support.

19. The ultrasonic diagnostic apparatus according to claim 12, wherein the driver is configured to drive, when one of the rotator and the linear motion part reaches the movement limit, the other of the rotator and the linear motion part while a single input operation of moving the operation panel is continuously performed.

* * * * *